United States Patent [19]

Yamada et al.

[11] Patent Number: 5,496,719
[45] Date of Patent: Mar. 5, 1996

[54] POLYPEPTIDE FROM HUMICOLA INSOLENS POSSESSING PROTEIN DISULFIDE ISOMERASE ACTIVITY GENE ENCODING THE SAME

[75] Inventors: Yukio Yamada, Tsushima; Osamu Asami, Kounan; Hidehiko Sugiyama; Chie Idekoba, both of Nagoya; Fumihiko Hoshino, Aichi; Masana Hirai, Seto; Tsutomu Kajino, Toyoake; Takao Imaeda, Kasugai; Kiyoko Sarai, Toyota, all of Japan

[73] Assignee: Kabushiki Kaisha Toyota Chuo Kenkyusho, Aichi, Japan

[21] Appl. No.: 68,395

[22] Filed: May 27, 1993

[30] Foreign Application Priority Data

May 27, 1992 [JP] Japan ............................. 4-135254
Mar. 4, 1993 [JP] Japan ............................. 5-044013
Mar. 4, 1993 [JP] Japan ............................. 5-044014

[51] Int. Cl.$^6$ ........................... C12N 9/90; C12N 9/00; A61K 38/00; C07K 1/00
[52] U.S. Cl. ........................ 435/233; 530/324; 530/350; 435/183
[58] Field of Search ............... 435/7.8, 191, 189, 435/6, 233, 91.1, 25, 69.1, 183; 530/350, 344, 371; 536/23.2, 25.4, 23.2; 935/14, 68

[56] References Cited

U.S. PATENT DOCUMENTS 4,889,818  12/1989  Gelfand et al. .................... 435/194
4,904,602   2/1990  Pigiet et al. ...................... 435/191

FOREIGN PATENT DOCUMENTS 2-460     1/1990  Japan .
4-197176  7/1992  Japan .

OTHER PUBLICATIONS

Gunther et al. J. of Biol. Chem. 268(11):7728 (1993).
Kaska et al. Biochem. J. 268:63 (1990).
Goldberger et al. J. of Biol. Chem. 238(2):628 (1963).
Edman et al. Nature 317:267 (1985).
Mizunga et al. J. Biochem. 108:846 (1990).
Tachikawa et al. J. Biochem 110:306 (1991).
LaMantia et al. P.N.A.S. 88:4453 (1991).
Scherens et al. Yeast 7:185 (1991).
Parkkonen et al. Biochem. J. 256:1005 (1988).
Yamauchi et al. Biochim & Biophy. Res. Comm. 146(3):1485 (1987).
Pihlajniemi et al. EMBO J. 6(3):643 (1987).
Gong et al. Nucleic Acid Res. 16(3)1203 (1988).

*Primary Examiner*—W. Gary Jones
*Assistant Examiner*—Bradley L. Sisson
*Attorney, Agent, or Firm*—Oblon, Spivak, McClelland, Maier & Neustadt

[57] ABSTRACT

A highly thermostable polypeptide possessing protein disulfide isomerase (PDI) activity, a gene coding for the polypeptide and a process for producing the polypeptide are provided. The polypeptide possessing PDI activity is characterized by A) having a capability of catalyzing a disulfide exchange in proteins, B) recognizing mainly ribonuclease A as a substrate, C) having a suitable active temperature of 20° to 70° C., D) being stable at a pH value of 6 to 9, and E) having a molecular weight of about 60,000 to 62,000. Since it has a higher thermostability and exhibits a stable activity in a wider dithiothreitol concentration range as compared with the conventional PDI, it is possible to provide a novel enzyme active protein which can be advantageously used for a refolding reaction of certain proteins. Further, a process which enables the polypeptide possessing PDI activity to be efficiently produced using *Humicola insolens* or a transformant transformed with an expression vector containing the above-described gene is also provided.

2 Claims, 7 Drawing Sheets

POLYPEPTIDE FROM HUMICOLA INSOLENS POSSESSING PROTEIN DISULFIDE ISOMERASE ACTIVITY GENE ENCODING THE SAME

TECHNICAL FIELD

The present invention relates to a polypeptide possessing protein disulfide-isomerase (hereinafter abbreviated to "PDI") activity and a process for producing the same. More particularly, it is concerned with a highly thermostable polypeptide possessing PDI activity produced by microorganisms belonging to the genus Humicola and a process for producing the same.

Further, it is concerned with a gene encoding the polypeptide possessing PDI activity and a derivative thereof, a transformant transformed with an expression vector into which the gene has been included, and a process for producing a polypeptide possessing PDI activity using said transformant.

BACKGROUND ART

In general, since PDI has a capability of catalyzing a disulfide exchange in proteins, the application thereof to, for example, refolding of recombinant proteins produced by utilizing, as a host, prokaryotic cells, such as *Escherichia coli* and *Bacillus subtilis*, have been studied in the art. The term "refolding" used herein is intended to mean that proteins incapable of exhibiting an inherent physiological activity due to erroneous bonding form of a disulfide bond are converted to an active type by correcting the bonding form of the disulfide bond.

Examples of conventional methods for refolding the recombinant protein inactive due to a deficiency of the disulfide bond include a method wherein use is made of a chemical redox reaction (see Japanese Unexamined Patent Publication (Kokai) No. 1-131195) and a method wherein use is made of PDI (see Japanese Unexamined Patent Publication (Kokai) No. 63-294796). Since PDI has been considered as an enzyme actually involved in the formation of a disulfide bond of proteins in vivo, the utilization of PDI in a reaction in vitro is a very rational conception.

Since PDI was first found by Anfinsen et al. as an enzyme capable of catalyzing the formation of a disulfide bond (see *J. Biol. Chem.*, 238, 628 (1963)), PDI is known to be widely distributed in several tissues of mammals and to exhibit a high activity particularly in organs wherein proteins having a disulfide bond are actively synthesized or secreted (such as liver, pancreas, spleen and lymphatic tissue) (see Hillson, D. A., Lambert, N., Freedman, R. B., *Methods in Enzymology*, 107, 281–294, 1984). In recent years, it has been found that PDI is present in, besides mammals, green algae (see Kaska, D. D., Kivirikko, K, I., Myllylae, R.: *Biochemical Journal*, 268, 63–68, 1990) and yeast (see Mizunaga, T., Katakura, Y., Miura, T., Marugama, Y., *Journal of Biochemistry*, 108, 846–851, 1990). Known features common to these PDI's are such that they has a molecular weight of 52,000 to 62,000, comprise a dimer comprising identical two subunits and an isoelectric point of 4.0 to 4.5. Further, the amino acid sequence of PDI has a feature that it has two sequences of (Trp-Cys-Gly-His-Cys-Lys; SEQ ID NO:4) considered as an active site in a subunit polypeptide chain.

PDI's per se and techniques for utilizing PDI in refolding of proteins have already been reported in the art (see Japanese Unexamined Patent Publication (Kokai) Nos. 4-197176; 2-460, 64-20086 and 63-294796). The PDI's used therein are derived from mammals and yeast, and have a problem of stability when they are used in the above-described purposes. For this reason, it is necessary to provide a polypeptide possessing PDI activity which has a significantly higher stability than the conventional PDI, can be used in a wide range of temperatures and is resistant to a sulfhydryl-group-containing reducing agent in a wide concentration range generally necessary to be added in a refolding reaction system, for example, dithiothreitol (hereinafter abbreviated to "DTT"). Further, the provision of such an active protein in turn leads to a desire for the development of a technique for mass-producing the active protein.

Accordingly, the first object of the present invention is to provide a polypeptide possessing PDI activity having a higher stability than conventional PDI's. The second object of the present invention is to provide a production process which enables PDI having a high stability to be mass-produced with a high efficiency.

SUMMARY OF THE INVENTION

The present inventors have aimed at fungi with considerations of the presence of active proteins derived from yeast and mammals and series of evolution from yeast to mammals although it is not known that fungi produce polypeptides possessing PDI activity. Especially, studies have been made on the polypeptide possessing PDI activity production capability of fungi capable of growing at a high temperature. As a result, one strain belonging to the genus Humicola produces polypeptides possessing PDI activity which has a better thermostability (that is, a higher upper limit of action temperature) than bovine PDI and is resistant to a sulfhydryl-group-containing reducing agent, for example, DTT, in a wide concentration range generally necessary to be added in a refolding reaction.

Further, the present inventors have made extensive and intensive studies on the amino acid sequence of polypeptides possessing PDI activity produced in the above-described manner. They have specifically amplified a part of the PDI gene by the PCR method based on the information obtained from the amino acid sequence, and the whole length of the PDI gene could be successfully cloned from cells of fungi by using the resultant DNA fragment as a probe. Further, they have found that proteins having a PDI activity can be produced by constructing a recombinant DNA containing the resultant gene and culturing a transformant transformed with the recombinant DNA.

Accordingly, according to the first aspect of the present invention, there is provided a highly thermostable polypeptide possessing protein disulfide isomerase (PDI) activity.

The polypeptide possessing PDI activity of the present invention is characterized by the following properties:

(A) it has a capability of catalyzing a disulfide exchange in proteins;

(B) it recognizes at least ribonuclease A as a substrate;

(C) it has a suitable action temperature of 20° to 70° C.;

(D) it is stable at a pH value of 6 to 9; and (E) it has a molecular weight of about 60,000 to 62,000 as measured by SDS-polyacrylamide gel electrophoresis.

As described above, since this polypeptide possessing PDI activity has a highly suitable action temperature and is resistant to DTT in a wide concentration range, when recombinant proteins are subjected to refolding, it is possible to set wider temperature and DTT concentration ranges as compared with known PDI's, which gives the polypeptide possessing PDI activity of the present invention considerable advantage.

Further, according to another aspect of the present invention, there is provided a structural gene containing a nucleotide sequence encoding the above-described polypeptide possessing PDI activity, or a derivative of the structural gene. In particular, among fungal polypeptides possessing PDI activity, the active proteins derived from one strain of *Humicola insolens* having a superior properties has an amino acid sequence represented by SEQ ID NO. 1 of SEQUENCE LISTING attached hereto, so that a gene having at least a nucleotide sequence encoding such amino acid sequence is preferred.

Further, according to a further aspect of the present invention, there is provided a process for producing the polypeptide possessing PDI activity which comprises culturing *Humicola insolens* or a transformant transformed with a vector containing the above-described gene or a derivative thereof, and recovering the polypeptide possessing PDI activity from the resulting cultured product.

DETAILED DESCRIPTION OF THE INVENTION

Figure 1:
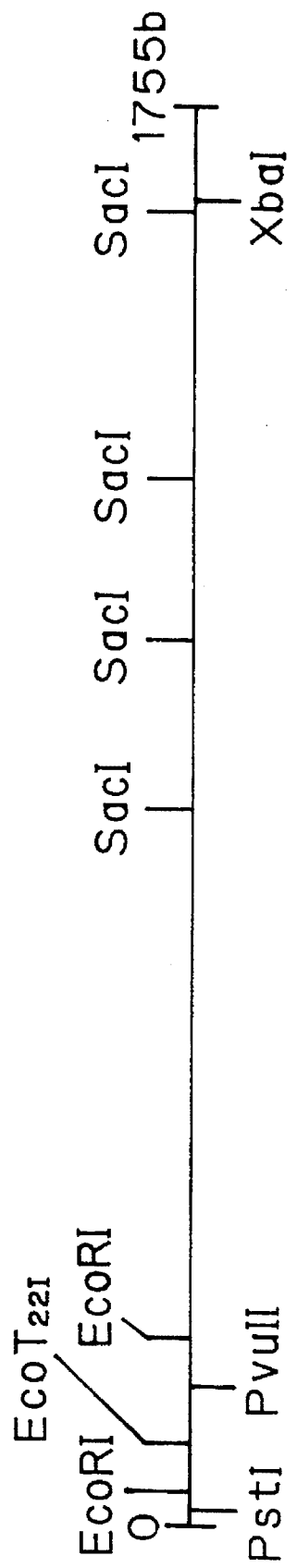
FIG. 1 is a schematic restriction map of a cDNA portion contained in a plasmid prepared in Example 5.

Although the polypeptide possessing PDI activity of the present invention is not limited by a harvest source and a production process, it can be advantageously produced, for example, by a production process using microorganisms belonging to the genus Humicola provided according to a further aspect of the present invention which will be described later. For example, the polypeptide possessing PDI activity produceable from *Humicola insolens* has an amino acid sequence represented by SEQ ID NO. 1 of SEQUENCE LISTING attached hereto and the following additional properties besides the above-described properties (A) to (E).

(F) conditions for inactivation by pH: although it is stable at pH 6 to 9 when incubated for 30 min, the activity is lowered to 70% at pH 5 and 40% at pH 10; and (G) inhibitors of the polypeptide possessing PDI activity: it is completely inactivated upon being exposed to 1 mM N-ethylmaleimide. Although it is stable against 0.2 mg/ml of bacitracin, the activity is lowered to 20% when the concentration is increased to 2 mg/ml.

The polypeptide possessing PDI activity was produced by adding alumina to cultured cells of *Humicola insolens*, extracted at neutral pH, centrifuged, applying the extract to DEAE-cellulose ion exchange chromatography and purifying an active fraction by concanavalin A affinity chromatography. The activity of the active protein was determined as follows. After a disulfide bond of a ribonuclease A (RNase-A) originated from bovine pancreas is once subjected to reduction cleavage, the cleaved sulfhydryl groups are again bonded to each other at a site different from the original bonding site to lose the enzyme activity of the ribonuclease (scrambling). The active protein is allowed to re-activate the scrambled ribonuclease A (hereinafter referred to as "SC-RNase A") as a substrate in the presence of DTT, and the decomposition of a ribonucleic acid with RNase-A activated as a result of refolding is determined. In this case, the activity of the polypeptide possessing PDI activity was determined by an increase in the absorbance ($A_{260}$).

More specifically, it was confirmed that the active protein of the present invention catalyzes the following three reactions.

a) A sulfhydryl group (—SH) in proteins is oxidized to a disulfide (—S—S—) bond in the presence of dissolved oxygen or oxidized glutathione (oxidation reaction).

b) A sulfhydryl group and a disulfide bond in proteins are exchanged with each other in the presence of DTT or reduced glutathione (isomerization reaction, refolding reaction).

c) A disulfide bond in proteins is reduced to a sulfhydryl group in the presence of DTT or reduced glutathione (reduction reaction).

Therefore, the polypeptide possessing PDI activity according to the present invention can be used in any reaction involving these reactions. However, the isomerization reaction (b) is the most promising reaction from the practical viewpoint. In recent years, proteins having disulfide bonds in its molecule have been mass-produced by genetic engineering techniques. In the production of this type, when prokaryotic cells, such as *Escherichia coli*, is used as a host, incorrect disulfide bonds are often formed, which leads to the production of inactive proteins. The polypeptide possessing PDI activity acts on these proteins so that native correct disulfide bonds are reconstructed, which enables the physiological activity inherent in the proteins to be recovered. The proteins have in their molecules a disulfide bond which is indispensable to the expression of the physiological activity, and examples thereof include ribonuclease A, insulin, aprotinin, human growth hormone, interferons ($\alpha$, $\beta$, $\gamma$), and so on.

As described above, the polypeptide possessing PDI activity of the present invention is superior in thermostability to the conventional PDI and, at the same time, has a wide effective concentration range with respect to the resistance to DTT or reduced glutathione coexistent in the isomerization reaction, which renders the polypeptide possessing PDI activity of the present invention advantageous for use in various applications.

The polypeptide possessing PDI activity can be produced by culturing a microorganism belonging to the genus Humicola in a nutrient broth and recovering a polypeptide possessing PDI activity from the cultured product.

The microorganism used in the present invention belongs to the genus Humicola, and any microorganism belonging to the genus Humicola may be used independently of the species so far as it has a capability of producing the above-described thermostable polypeptide possessing PDI activity. For example, it is preferred to use a strain that has been isolated by the present inventors from soil near the headspring of the spa of Jigokudani in Kumamoto, Japan, identified as *Humicola insolens* KASI, deposited as FERM P-12911 on Apr. 2, 1992 with the Patent Microorganism Depository, Fermentation Research Institute, Agency of Industrial Science and Technology, Ministry of International Trade and Industry, Japan and then transferred to and deposited as FERM BP-4239 under Budapest Treaty with the International Depositary Authority of said Patent Microorganism Depository. The FERM BP-4239 strains were inoculated into a malt extract agar plate culture medium, a potato dextrose agar plate culture medium and a YpSs agar plate culture medium and incubated at 25° C., 37° C., 43° C. or 50° C. for 3 to 14 days, and the color tone, tissue and conidiogenesis of the grown colony of fungi were observed. As a result, the colony exhibited the following mycological properties, and the strain was identified as *Humicola insolens* by reference to D. G. Cooney and R. Emerson, "Thermophilic Fungi", 72–79 (1964) (published by W. H. Freeman and Company) by its taxonomic properties.

| Properties of FERM BP-4239 | |
|---|---|
| Item | Properties (YpSs agar plate culture medium) |
| Growth rate | Diameter of colony: 3–4 cm (37° C., 3 days) |
| Growth at 50° C. | Growable |
| Color of surface of colony | White-graysh brown |
| Conidiogenesis | Formed in middle and tip of hypha and on short branch extended from hypha in single or chain manner |
| Conidium form | Subspherical-elliptical-flask form |

Culture of this strain in a nutrient broth commonly employed in the culture of fungi enables the polypeptide possessing PDI activity of the present invention to be produced with a high efficiency.

The polypeptide possessing PDI activity thus produced was confirmed to have an amino acid sequence represented by SEQ ID No. 1 of SEQUENCE LISTING attached hereto by the sequence determination for the corresponding nucleotide sequence and amino acid sequence which will be described later. Therefore, the present invention provides a polypeptide possessing PDI activity containing such an amino acid sequence and a gene encoding the sequence or a derivative thereof.

One example of the gene is a gene containing at least a sequence from nucleotide 170 (the first nucleotide T of a codon coding for Ser (+1) in an amino acid sequence described together with the nucleotide sequence) to nucleotide 1624 (beginning with the Ser of the amino acid sequence and ending with the third nucleotide T of the codon coding for Leu which is the 485th amino acid in the amino acid sequence described together with the nucleotide sequence) in a nucleotide sequence represented by SEQ ID NO. 2 of SEQUENCE LISTING. Specific examples of the gene containing a further nucleotide sequence include a gene having a nucleotide sequence comprising the nucleotide sequence 170 to 1624 represented by SEQ ID No. 2 and, added upstream of the 5' end thereof, translation initiation codon ATG or a sequence from nucleotide 110 (the first nucleotide A of codon coding for Met of amino acid sequence-20) to nucleotide 169 (the third nucleotide C of codon coding for Ala of amino acid sequence-1) contained in the nucleotide sequence represented by SEQ ID No. 2. Further, a gene comprising the nucleotide sequence 170 to 1624 represented by SEQ ID No. 2 and, added upstream of the 5' end thereof, GAC or ATCGAC as well falls within the scope of the present invention.

The derivative of these genes are not particularly limited so far as the polypeptide produced by expression of the derivative has a desired PDI activity. Examples of the derivative include a gene comprising the above-described nucleotide sequence 170 to 1624 wherein some region thereof produceable by a known method has been substituted or deleted or a given oligonucleotide has been newly inserted thereinto. Further, it is a matter of course that the gene of the present invention embraces a gene comprising a variant wherein the nucleotide of the nucleotide sequence 170 to 1624 has been changed in a acceptable wobble range of codon, that is, to such an extent that the amino acid sequence represented by SEQ ID No. 1 is not varied, and derivatives of such a gene. Therefore, the expression "a sequence having an activity equivalent to that of the amino acid sequence represented by SEQ ID No. 1" used in the present invention is intended to mean the amino acid sequence of a polypeptide produced by the expression of the above-described derivative.

Further, according to the present invention, there is provided a transformant transformed with a vector containing the above-described gene or a derivative thereof. In this case, the vector is preferably an autonomous replicative vector, that is, the so-called "expression vector".

The transformant can be prepared, for example, by the following method. Specifically, the transformant can be prepared by (i) isolating mRNA encoding the PDI from fungal cells, (ii) synthesizing from the RNA a single stranded complementary DNA (cDNA) and then a double stranded DNA, (iii) incorporating the complementary DNA into a phage or a plasmid, (iv) transforming a host with the resultant recombinant phage or plasmid, (v) culturing the transformant and isolating a phage or plasmid containing an intended DNA from the transformant by a suitable method, for example, immunoassay using an anti-fungal PDI antibody or a plaque hybridization or a colony hybridization using a probe labeled with a radioactive isotope, (vi) sectioning an intended cloned DNA from the phage or plasmid, and (vii) ligating the cloned DNA downstream of a promoter in the vector and effecting transformation using this expression vector.

Examples of methods for preparing RNA from cells include a guanidine thiocyanate method [see *Biochemistry*, 18, 5294 (1979)]. cDNA is synthesized using a reverse transcriptase with the resultant RNA being used as a template, for example, by a method established by Gubler et al. [see *Gene*, 25, 263 (1983)], and the resultant cDNA is incorporated into a plasmid or a phage. Examples of the plasmid into which the cDNA is incorporated include plasmids derived from *Escherichia coli* such as pBR322 [see *Gene*, 2, 95 (1977)], pBR325 [see *Gene*, 4, 121 (1978)], pUC12 [see *Gene*, 19, 259 (1982)] and pUC13 [*Gene*, 19, 259 (1982)], and plasmids derived from *Bacillus subtilis* such as pUB110 [see *Biochem. Biophys. Res. Commun.*, 112, 678 (1983)], and some of them are commercially available. Other plasmids may be used so far as they can be replicated and held within hosts. On the other hand, examples of the phage vector into which the cDNA is incorporated include λgt 11 [see *Proc. Natl. Acad. Sci. USA*, 80, 1194 (1983)] and λZapII (available from Stratagene), and any of other phage vector may be used so far as they can be autonomously replicated in hosts. Examples of methods for incorporating cDNA into the plasmid include a method described in, for example, *Molecular Cloning*, 2nd Ed. Cold Spring Harbor Laboratory (1989). Examples of methods for incorporating cDNA into the phage vector include a method described in, for example, *DNA cloning, a practical approach*, 1, 49 (1985). The plasmid or phage vector thus produced can be introduced into suitable hosts, which are easily available to a person with ordinary skill in the art, for example, *Escherichia coli* and *Bacillus subtilis*, to provide a transformant.

Examples of the above-described *Escherichia coli* include *Escherichia coli* K12 DH1 [see *Proc. Natl. Acad. Sci. USA*, 60, 160 (1968)], *Escherichia coli* JM105 [see *Nucl. Acids. Res.*, 9, 309 (1981)], *Escherichia coli* JA221 [see *J. Mol. Biol.*, 120, 517 (1978)], *Escherichia coli* HB101 [see *J. Mol. Biol.*, 41, 459 (1969)] and *Escherichia coli* C600 [see *Genetics*, 39, 440 (1954)]. Examples of the *Bacillus subtilis* include *Bacillus subtilis* MI114 [see *Gene*, 24, 255 (1983)] and *Bacillus subtilis* 207-21 [see *J. Biochem.* 95, 87 (1984)].

Examples of methods for transforming hosts with a plasmid include a calcium chloride method or a calcium chloride/rubidium chloride method described in Maniatis. T et al., *Molecular Cloning*, 2nd Ed., Cold Spring Harbor Laboratory (1989). The phage vector can be introduced into proliferated *Escherichia coli*, for example, by an in vitro packaging method. An intended clone is screened from the resultant transformants by known methods, for example, colony hybridization [see *Gene*, 10, 63 (1980)], plaque hybridization [see *Science*, 196, 180 (1977)] and DNA nucleotide sequencing [see *Proc. Natl. Acad. Sci. USA*, 74, 560 (1977)]. Thus, microorganisms bearing a vector having a DNA containing a nucleotide sequence encoding the cloned PDI can be obtained.

Then, a plasmid or a phage vector is isolated from these microorganisms. The isolation can be effected, for example, by alkaline extraction [see *Nucl. Acids. Res.* 1, 1513 (1979)]. The plasmid or phage vector having a DNA containing a nucleotide sequence encoding the cloned PDI can be used as it is or after digestion with a restriction enzyme. The cloned gene can be ligated downstream of a promoter in a vector suitable for expression, thereby providing an expression vector. Examples of the vector include the above-described plasmids derived from *Escherichia coli* (for example, pBR322, pBR325, pUC12, pUC13 and ptrp781), the above-described plasmids derived from *Bacillus subtilis* (for example, pUB110, pTM5 and pC194), the above-described plasmids derived from yeast (for example, pSH19, pSH15, pGLD906, pGLD906-1, pCDX and pKSV- 10), bacteriophage, such as λ phage, and animal virus, such as retrovirus and vaccinia virus.

As described above, the gene according to the present invention may have ATG as a translation initiation codon at its 5' end and TAA, TGA or TAG as a translation termination codon at its 3' end. Further, in expressing the gene, a promoter may be ligated upstream of the gene. Any promoter may be used in the present invention so far as it properly corresponds to hosts used in the expression of the gene. When the host used in the transformation is *Escherichia coli*, use may be made of trp promoter, lac promoter, rec promoter, $\lambda P_L$ promoter, lpp promoter, etc. On the other hand, when the host is *Bacillus subtilis*, use may be made of SPO1 promoter, SPO2 promoter, penp promoter, etc., while when the host is yeast, p1105 promoter, PGK promoter, GAP (GLD) promoter, ADH promoter, etc. may be conveniently used. When the host is animal cells, use may be made of a promoter derived from SV40, a promoter of retrovirus, etc.

The vector containing the gene or derivative thereof according to the present invention thus produced is used to produce a transformant. Examples of the host include prokaryotic organisms, such as *Escherichia coli*, *Bacillus subtilis* and actinomycetes, and eukaryotic organisms, such as yeast, fungi and animal cells, which are easily available to a person with ordinary skill in the art. Specific examples of the *Escherichia coli* and *Bacillus subtilis* are the same as those described above. Specific examples of the yeast include *Saccharomyces cerevisiae* AH22, *Saccharomyces cerevisiae* AH22R- and *Saccharomyces cerevisiae* NA87-11A and *Saccharomyces cerevisiae* DKD-5D. Specific examples of the animal cells include monkey cells COS-7, Vero, Chinese hamster cells and mouse L cells. The *Escherichia coli* can be transformed, for example, by methods described in *Proc. Natl. Acad. Sci. USA*, 69, 2110 (1972) and *Gene*, 17, 107 (1982). The yeast can be transformed, for example, by a method described in *Proc. Natl. Acad. Sci. USA*, 75, 1929 (1978). The animal cells can be transformed, for example, by a method described in *Virology*, 52, 456 (1973).

Thus, a transformant transformed with a vector containing the gene or derivative thereof according to the present invention can be provided.

Further, according to the present invention, there is provided a polypeptide possessing PDI activity characterized by being produced by culturing the above-described transformant in a nutrient broth, producing and accumulating in the culture a protein containing the above-described amino acid sequence or a sequence equivalent in terms of the activity to the amino acid sequence, and recovering the protein.

Therefore, according to the present invention, there is provided a process for producing a polypeptide possessing PDI activity using the above-described microorganism belonging to the genus Humicola or using the above-described transformant.

When use is made of a strain belonging to the genus Humicola, the nutrient medium used in the culture may be a culture medium commonly used in the culture of eumycetes. Although the culture medium may be any of a solid medium and a liquid medium, the liquid medium is preferred from the viewpoint of harvesting cells. Specific examples of the medium include a malt extract medium, a potato glucose medium and a Czapek medium. The culture is preferably effected under conditions of a culturing temperature of 30° to 50° C. (the maximum growable temperature being 50° C.) for a period of 3 to 6 days.

When use is made of the above-described transformant, if the host is *Escherichia coli*, *Bacillus subtilis*, actinomycetes, yeast or fungi, a liquid medium is suitable for use as the nutrient broth used in the culture. A carbon source, a nitrogen source, an inorganic source and, if necessary, a trace metal or vitamin are added to the liquid medium, or an antibiotic contributing to the selection of a host when the host has a selection marker. Examples of the carbon source include glucose, dextrin, soluble starch and sucrose, examples of the nitrogen source include inorganic or organic substances, such as ammonium salts, nitrates, peptone and meat extracts, and examples of the inorganic substance include calcium chloride, sodium phosphate and magnesium chloride. More specifically, when the host is *Escherichia coli*, the culture medium is preferably M9 medium containing, for example, glucose and casamino acid [see *J. Exp. Mol. Genet.* p. 431, Cold Spring Harbor Laboratory, New York. 1972]. In this case, the cultivation is usually effected at 14° to 43° C. for about 3 to 24 hr optionally with aeration or stirring. When the host is *Bacillus subtilis*, the culture using the medium is usually effected at 30° to 40° C. for about 6 to 24 hr optionally with aeration or stirring. When the host is yeast, examples of the medium used include Burkholder minimal medium [see *Proc. Natl. Acad. Sci. USA*, 77, 4505 (1980)] and low Pi medium [see *Biochem. Biophys. Res. Commun.* 138, 268 (1986)]. The pH value of these media is preferably adjusted to about 5 to 8. In this case, the cultivation is usually effected at about 20° to 35° C. for about 24 to 72 hr optionally with aeration or stirring. When a transformant using animal cells as the host is cultured, examples of the medium used include MEM medium containing about 5 to 20% of fetal bovine serum [see *Science.* 122, 501 (1952)] and RPMI1640 medium [see *J. Am. Med. Assoc.* 199, 519 (1967)]. The pH value is preferably about 6 to 8. The culture is usually effected at about 30° to 40° C. for 15 to 60 hr optionally with aeration or stirring.

The polypeptide possessing PDI activity of the present invention is produced and accumulated within or outside the cells. The extraction of the intracellular protein from the cultured product is effected by a method which comprises collecting cells by a known method after the culture, suspending the cells in a buffer containing a protein denaturant, such as guanidiun chloride or urea, or a buffer containing a detergent, such as Triton X-100 (trademark), and obtaining a supernatant containing the protein by centrifugation, or a method which comprises crushing with glass beads, an ultrasonic treatment, or a treatment with an enzyme, such as lysozyme, or a freeze and thawing method and providing a supernatant containing an intended protein by centrifugation. The protein produced and accumulated in the supernatant or outside the cells can be isolated and purified by a combination of known isolation and purification methods. Examples of the isolation and purification methods include a salting-out or a solvent precipitation wherein a difference in the solubility is utilized, a dialysis, an ultrafiltration or a gel filtration wherein a difference in the molecular weight is utilized, an ion exchange chromatography wherein a difference in the charge is utilized, an affinity chromatography wherein a specific affinity is utilized, a reversed phase high performance liquid chromatography wherein a difference in the hydrophobicity is utilized, and a hydroxyapatite chromatography wherein a specific adsorption is utilized.

The polypeptide produced by the process according to the present invention has a capability of catalyzing an exchange reaction between sulfhydryl group and disulfide bonds present in any protein to form a disulfide bond of the native type. More specifically, the polypeptide catalyzes such a reaction that it acts on a reduced protein or an oxidized protein having a non-native disulfide bond in the presence of dissolved oxygen, an oxidized glutathione (GSSG)/reduced glutathione (GSH) mixture or a reducing agent, such as dithiothreitol (DTT) or 2-mercaptoethanol (2-ME), to again form a disulfide bond of the native type. Therefore, the polypeptide produced according to the present invention can be preferably used for the purpose of efficiently forming a disulfide bond of the native type in the protein molecule in the production of a polypeptide having a disulfide bond in its molecule using a gene recombinant technique especially when prokaryotic cells, such as *Escherichia coli* or *Bacillus subtilis*, are used as the host for the recombinant DNA. Examples of the polypeptide include cytokines, such as interferon-α, interferon-β, interferon-γ, interleukin-1, interleukin-2, macrophage activating factors and lymphotoxins, peptide hormones, such as transforming growth factors, erythropoietin, epithelial growth factors (EGF), fibroblast growth factors (FGF), insulin and human growth hormones, pathogenic microorganism antigen proteins, such as hepatitis B virus antigen, enzymes, such as peptidase and lysozyme, and blood protein components, such as human serum albumin and immunoglobulin.

The active polypeptide of the present invention used for the treatment of the above-described polypeptide may be in a highly purified grade or a partially purified grade. The active polypeptide of the present invention can directly act on the protein to be treated in such a state that it is intracellularly or extracellularly produced and accumulated, or in the form of a purified preparation. Further, the polypeptide of the present invention can be used as a water-soluble enzyme. Moreover, it may be used with it being immobilized on a suitable carrier. Further, it is also possible to effect the treatment for again forming the disulfide bond of the protein by using a transformant produced by doubly infecting the transformant of the present invention with a recombinant DNA encoding the active polypeptide. In the specification and accompanying sequence listings and drawings, use is made of the following abbreviations:

PBS: phosphate buffer
DNA: deoxyribonucleic acid (DNA)
cDNA: complementary deoxyribonucleic acid
A: adenine
T: thymine
G: guanine
C: cytosine
RNA: ribonucleic acid (RNA)
mRNA: messenger RNA
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Lys: lysine
Arg: arginine
His: histidine
Phe: phenylalanine
Tyr: tyrosine
Trp: tryptophan
Pro: proline Asn: asparagine Gln: glutamine Polypeptide containing a sequence having an equivalent activity produced by the process according to the present invention may be such that a part (up to about 5%) of the amino acid sequence is added, deleted or replaced with another amino acid.

The present invention will now be described in more detail with reference to the following Reference Examples and Examples, though it is not limited to these Examples only.

Example 1: Cultivation

*Humicola insolens* KASI (FERM BP-4239) grown on a potato dextrose agar medium was inoculated into a plate containing a malt extract liquid medium. The mixture was cultivated at 50° C. for 4 to 6 days. Fungal cells grown on the surface of the medium were collected on gauze and washed with water to remove the medium components deposited on the cells.

Example 2: Extraction and Purification of Polypeptide Possessing PDI Activity from Fungal Cells To 20 g of the fungal cells provided in Example 1 were added an extracting solution (containing 20 mM sodium phosphate buffer (pH 7), 10 mM ethylenediaminetetraacetic acid, 1 mM phenylmethylsulfonic acid fluoride, 1 mM tosyllysine chloromethyl ketone, 50 µg/ml aprotinin and 50 µg/ml soybean trypsin inhibitor) in an amount of 10 times the amount of the fungal cells. A suitable amount of alumina was added thereto, and the mixture was subjected to grinding extraction in a mortar. The extraction was centrifuged at $1 \times 10^4$ g for 10 min, and the supernatant was taken out and applied to a DEAE-cellulose column equilibrated with 20 mM sodium phosphate buffer (pH 7.5) and 10 mM ethylenediaminetetraacetic acid (EDTA) (column volume=10 ml, flow rate=20 ml/hr) and then washed. After a nonadsorbed fraction was eluted with the same buffer as described just above, a linear gradient elution was effected with a solution comprising the same buffer as described just above and, added thereto, 0.5M NaCl.

Fractions having a PDI activity were collected, and applied to a concanavalin A-Sepharose column (column volume= 1 ml, flow rate=10 ml/hr) equilibrated with 20 mM Tris-HCl buffer and 0.5M Nacl, pH 7.5. After the column was washed with the same buffer as described just above, elution was effected with a solution comprising the same buffer as described just above and, added thereto, 0.5M α-methyl mannoside. The eluate had an PDI activity, and about 20 µg of a polypeptide possessing PDI activity was obtained from 20 g of the fungal cells.

Further, the PDI active fraction was purified by reversed phase high performance liquid chromatography. Specifically, a reverse phase column comprising a polymer base and a butyl group bonded to the base (C4P-50 manufactured by Asahi Kasei Kogyo K.K.) was previously equilibrated with 10 mM ammonium acetate buffer (pH 7), and a concanavalin A-Sepharose eluting solution containing a PDI activity was applied to the column. After washing the column, the polypeptide possessing PDI activity was eluted with acetonitrile in the eluting solution being linearly increased. The polypeptide possessing PDI activity obtained up to this stage was analyzed by SDS-polyacrylamide electrophoresis. As a result, the active polypeptide exhibited a single band which showed that it was a pure product. The molecular weight was calculated based on the mobility of a marker having a known molecular weight subjected to migration together with the active polypeptide and found to be 60,000 to 62,000.

Thus, 12 µg of a PDI active polypetede as a pure product was finally obtained from 20 g of the fungal cells. The whole amino acid sequence of the PDI derived from *Humicola insolens* KASI (FERM BP-4239) was determined by analysis of restriction cleavage product of the above-described protein and by reference to cDNA sequence etc. which will be described later. The results are provided in SEQ ID No. 1 of SEQUENCE LISTING attached hereto.

Example 3: Preparation of cDNA Library Derived from mRNA of Humicola insolens

The total RNA was extracted from cells of *Humicola insolens* (FERM BP-4239) (hereinafter referred to simply as "fungi") by the guanidine isocyanate method (see Chirgvin, J. V. et al., *Biochemistry*, 18, 5294 (1979)), and poly(A)RNA was purified from the RNA by oligo-dT cellulose column chromatography (manufactured by Pharmacia). cDNA was prepared using the poly(A)RNA as a template by a method established by Gubler, U and Hoffman, B. J. (see *Gene*, 25, 263 (1983)). After an EcoRI/NotI adaptor (cDNA Synthesis Kit manufactured by Pharmacia) was added thereto, the cDNA was cloned at the EcoRI site of λZAPII (manufactured by Stratagene) to provide a cDNA library.

Example 4: Specific Amplification of Fungal PDI Gene by RT-PCR Method

The fungal PDI gene was specifically amplified by using an RNA PCR Kit (manufactured by Takara Shuzo Co., Ltd.). The detailed procedure was effected according to the protocol of the maker. cDNA was synthesized by using as the template the total RNA extracted from the fungi and ****as the primer a random hexamer. Then, PDI gene was specifically amplified by using as the template the resultant cDNA and as the primer an oligonucleotide synthesized based on a part of amino acid sequence (see SEQ ID No. 1; Lys Asp Thr Phe Asp Asp Phe Ile (SEQ ID No:5) and Glu Val Gly His Gln Gln Cys (SEQ ID NO:6)) of the purified PDI active polypeptide described in the reference example. The sequences of the primers were as follows.

| Peptide (SEQ ID NO: 5):<br>Primer ①: 5' - GGGAATTC | Lys<br>AAA<br>G | Asp<br>GAT<br>C | Thr<br>ACA<br>G<br>C<br>T | Phe<br>TTT<br>C | Asp<br>GAT<br>C | Asp<br>GAT<br>C | Phe Ile<br>TTT AT - 3' (SEQ ID NO: 7)<br>C |
|---|---|---|---|---|---|---|---|
| Peptide:<br>Primer ②: 5' - GGGAATTC | Glu<br>TC | Val<br>AAC<br>G<br>C<br>T | Gly<br>ACC<br>G<br>C<br>T | His<br>ATG<br>G | Gln<br>TTG<br>C | Gln<br>TTG<br>C | Cys (SEQ ID NO: 6)<br>ACA - 3' (SEQ ID NO: 8)<br>G |

The primers were synthesized by a DNA synthesizer (manufactured by Applied Biosystems Inc., U.S.A.). An about 0.2 kbp DNA was specifically amplified by the PCR method. When the DNA fragment was digested with restriction enzyme EcoRI, it was cleaved into two fragments, that is, about 50 bp and 150 bp fragments. Each DNA fragment was cloned at the EcoRI site of plasmid pUC118 to provide plasmid pUC118ΔPDI-1 and pUC118ΔPDI-2. *E. coli* JM109 was transformed with these plasmids (see Messing, J., *Gene*, 33, 119 (1985)), and the transformants were subjected to screening to provide clone JM109/pUC118ΔPDI-1 and clone JM109/pUC118ΔPDI-2 each containing an intended plasmid. Subsequently, plasmid pUC118ΔPDI-1 and plasmid pUC118ΔPDI-2 were extracted and purified from the provided JM109/pUC118ΔPDI-1 and JM109/pUC118ΔPDI-2 by the alkaline method [see Birnboim, H. C. and Doly, J., *Nucl. Acids Res.*, 11, 1513 (1979)].

Example 5: Isolation of Clone Containing Fungal PDI Gene and Determination of Nucleotide Sequence of The Gene

*E. coli* XL-1 Blue was infected with the cDNA library provided in Example 1, about 4000 transformed plaques in total were formed on an LB agar medium and transferred on a nylon filter (Hybond-N manufactured by Amersham), and recombinant DNA exposed and denatured in a 0.5N NaOH solution was subjected to UV immobilization on the filter (see Maniatis et al., *Molecular Cloning* 2nd Ed. Cold Spring Harbor Laboratory, 1989).

Separately, a DNA fragment prepared by cleaving the plasmid pUC118ΔPDI-2 described in Example 4 with restriction enzyme EcoRI was labelled with digoxigenin using a DNA Tailing Kit (manufactured by Beohringer) according to the protocol of the maker to provide a probe.

A clone reactive with the labelled probe was found from the filter on which recombinant DNA had been immobilized by using a DIG-ELISA Detection Kit (manufactured by Beohringer) according to the protocol of the maker. An insert fragment of positive clone λZAPIIPDI-2 provided by this method was subjected to subcloning into plasmid BluescriptSK(−) (manufactured by Stratagene) by the in vivo excision method (Stratagene) to provide plasmid pBluePDI-2. *E. coli* XL-1 Blue was transformed with the plasmid pBlue PDI-2. The plasmid pBluePDI-2 was extracted and purified from the resultant transformant XL-1 Blue/pBluePDI-2 by the above-described alkaline method. The cDNA portion contained in this plasmid had a total length of about 1.7 kbp, and a schematic restriction enzyme map thereof is shown in FIG. 1.

The nucleotide sequence of the cDNA portion was determined by the dideoxy method (see Sanger, F. et al., *Proc. Natl. Acad. Sci.*, 74, 5463 (1977)). The determined nucleotide sequence and the whole amino acid sequence estimated therefrom are provided in SEQ ID No. 2 of SEQUENCE LISTING attached hereto.

Example 6: Construction of Fungal PDI Gene Expression Plasmid for *Escherichia coli*

The plasmid pBluePDI-2 containing fungal PDIcDNA provided in Example 5 was cleaved with restriction enzymes PvuII and XbaI to provide a 1.4 kbp DNA fragment containing a region encoding the fungal PDI. Separately, plasmid pTrc99A (manufactured by Pharmacia) having a trc promoter and a lac regulator was cleaved with restriction enzyme NcoI, and synthetic oligonucleotides, i.e., 5' CATGTCGGATGTTGTCCAG 3' (SEQ ID NO:9) and 5' CTGGACAACATCCGA 3'. (SEQ ID NO:10), were ligated thereto with a T4DNA ligase to provide an about 4.2 kbp DNA fragment. Then, the DNA fragment was cleaved with restriction enzyme XbaI, and an about 4.2 kbp DNA fragment containing a trc promoter, an ampicillin-resistant gene and a plasmid replication initiation site was isolated.

Figure 2:
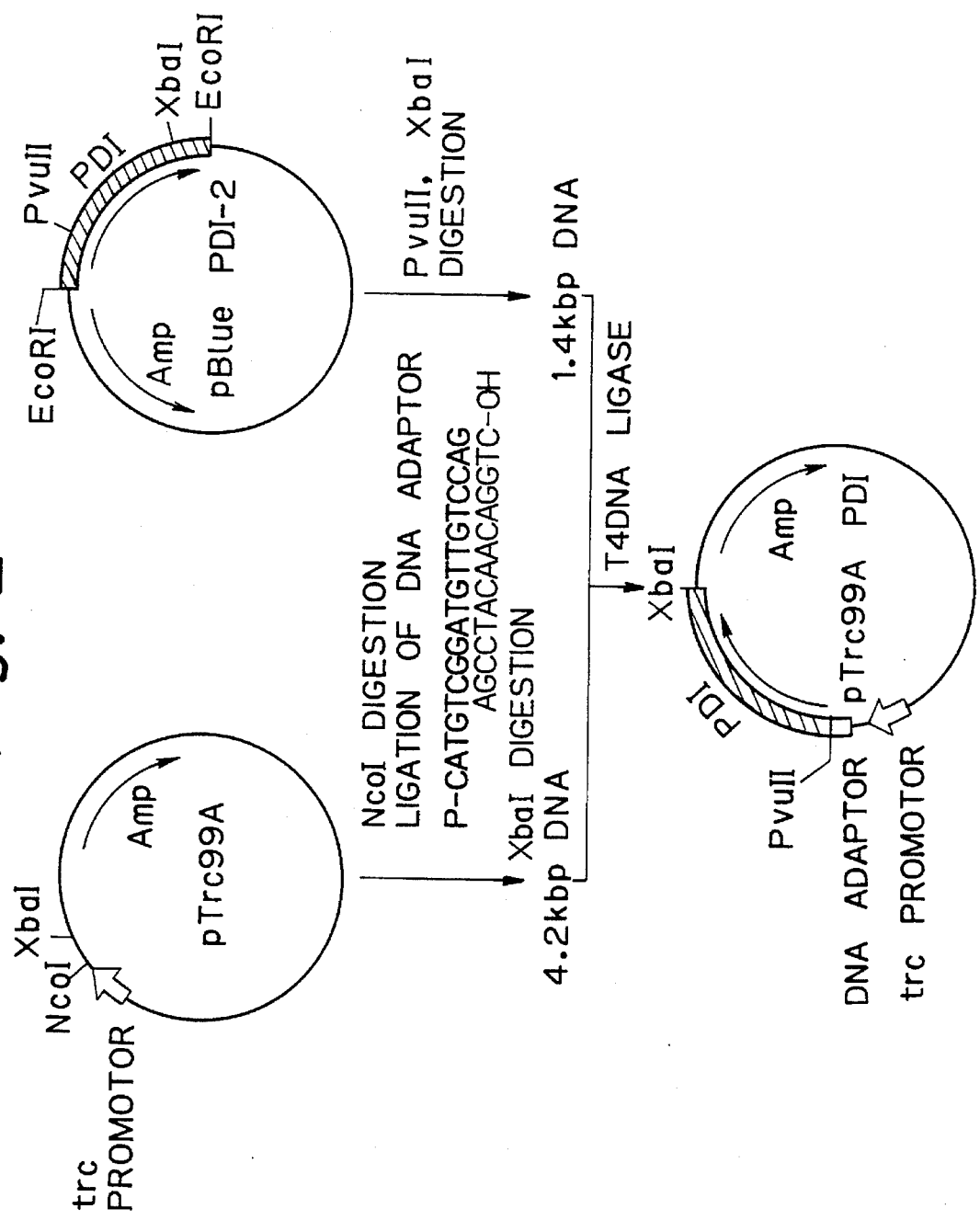
FIG. 2 is a procedure for constructing plasmid pTrc99APDI prepared in Example 6.

The 1.4 kbp PvuII-XbaI fragment containing a fungal PDI gene and the 4.2 kbp DNA fragment were ligated to each other with a T4DNA ligase to construct a fungal PDI expression plasmid pTrc99APDI (see FIG. 2). *E. coli* JM105 was transformed with this plasmid to provide transformant *E. coli* JM105/pTrc99APDI containing plasmid pTrc99APDI.

Example 7: Expression of Fungal PDI Gene in *Escherichia coli*

The transformant *E. coli* JM105/pTrc99APDI provided in Example 6 and *E. coli* JM105/pTrc99A as a control were cultivated at 37° C. in a culture medium comprising 10 g/liter Bacto trypton, 5 g/liter Bacto yeast extract, 10 g/liter sodium chloride and 50 mg/liter ampicillin. In this case, when the $OD_{600}$ was 1.0, IPTG (isopropyl-β-D-thiogalactoside) was added to a concentration of 5 mM, followed by cultivation for additional 3 hr.

The culture medium was centrifuged to collect cells which were washed with a 50 mM Tris-HCl (pH 7.4) solution in an amount of 0.5 times that of the culture medium, suspended in a minor amount of $H_2O$. An equal amount of 2× SDS gel-loading buffer (see Maniatis et al., *Molecular Cloning*, 2nd Ed., Cold Spring Harbor Laboratory (1989)) was added thereto, and the mixture was treated at 100° C. for 5 min, sonicated and centrifuged to provide a cell extract.

The cell extract was electrophoresed on an SDS-polyacrylamide gel, and an antigenic band was detected using an anti-fungal PDI antibody by the Western blotting method to confirm that a fungal PDI was formed.

Example 8: Purification of PDI Derived from *E. coli* JM105/pTrc99APDI

The *E. coli* JM105/pTrc99APDI containing fungal PDI expression plasmid pTrc99APDI provided in Example 6 was cultivated at 37° C. for 12 hr in one liter of a culture medium comprising 10 g/liter Bacto trypton, 5 g/liter Bacto yeast extract, 10 g/liter sodium chloride and 50 mg/liter ampicillin. The culture was transferred to 20 liters of an M-9 medium containing 10 g/liter glucose, 10 g/liter casamino acid and 2 mg/liter vitamin $B_1$ and further cultivated with aeration and stirring at 37° C. for 9 hr. Then, IPTG was added thereto to a concentration of 5 mM, followed by culturing for additional 4 hr. The culture was centrifuged to provide 320 g of cells.

30 g of the cells were homogeneously suspended in 150 ml of a 20 mM sodium phosphate buffer (pH 7.5) containing 10 mM EDTA and 1 mM PMSF, and the suspension was sonicated at 0° C., 5 times each for 1 min. Thereafter, the treated suspension was centrifuged to provide 145 ml of a cell extract. The cell extract was applied to a DEAE-cellulose column (2.5×10 cm, 50 ml) equilibrated with a 20 mM sodium phosphate buffer (containing 10 mM EDTA, pH 7.5), and elution was then effected. After the column was washed with the same buffer as described just above, a linear gradient elution was effected with a solution comprising the same buffer as described just above and, added thereto, 0.5M NaCl. Fractions having a PDI activity were collected, and ammonium sulfate was added thereto to a concentration of 1M. The mixture was added to a Butyl-Toyo Peal column (2.3×5 cm, 20 ml) equilibrated with a 20 mM sodium phosphate buffer (pH 7.5) containing 1M ammonium sulfate and 10 mM EDTA, and the column was washed with the same buffer as described just above. Thereafter, a linear gradient elution was effected with the same buffer solution as described above except that ammonium sulfate was not contained in the solution. Fractions having a PDI activity were collected and dialyzed against a 10 mM sodium phosphate buffer (pH 7.0) containing 0.15M sodium chloride and 10 mM EDTA overnight, and adsorbed on a hydroxylapatite column (HA-1000; 0.75×7.5 cm; manufactured by Tosoh Corporation) equilibrated with the same buffer as described just above. Then, the column was washed with the same buffer as described just above, and a polypeptide having a fungal PDI activity was eluted by a linear gradient elution with a 0.4M sodium phosphate buffer (pH 7.0) containing 0.15M sodium chloride and 10 mM EDTA. Fractions having a fungal PDI activity were dialyzed against a 20 mM Tris-HCl buffer (pH 8.0) containing 10 mM EDTA overnight, and adsorbed on a mono-Q column (0.5×5 cm; manufactured by Pharmacia) equilibrated with the same buffer as described just above. Then, the column was washed with the same buffer as described just above, and a polypeptide having a fungal PDI activity was eluted by a linear concentration gradient elution with a solution comprising the same buffer as described just above and, added thereto, 0.5M sodium chloride. Thus, 0.8 mg of a purified preparation of the polypeptide possessing PDI activity (protein concentration= 0.4 mg/ml, volume=2 ml) was obtained.

Example 9: Chemical Properties of Fungal PDI

The chemical properties of fungal PDI provided in Example 2 were examined.

(1) Molecular Weight

Figure 3:
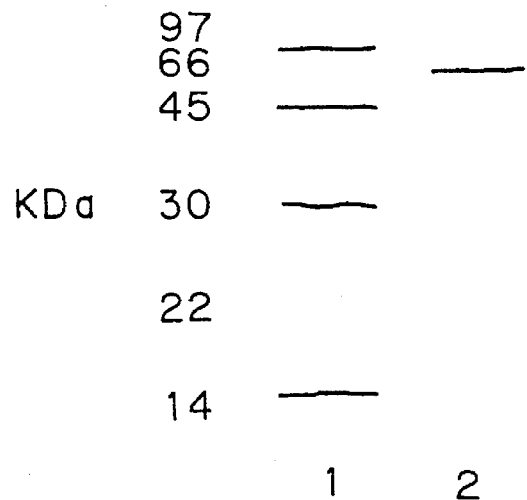
FIG. 3 is an electrophoretic pattern of SDS-polyacrylamide gel electrophoresis of a protein having a PDI activity in Example 8.

The PDI was electrophoresed on an SDS-polyacrylamide slab gel under 2-mercaptoethanol reduction conditions [see *Nature*, 227, 680 (1970)] and stained with Coomassie-Brilliant Blue R250. As a result, the polypeptide having a fungal PDI activity exhibited a band at a position corresponding to a molecular weight of about 60,000 dalton (see FIG. 3) (molecular weight of controls: bovine serum albumin=66 kDa, ovalbumin=45 kDa, carbonic anhydrase= 30 kDa, soybean trypsin inhibitor=22 kDa, and lysozyme= 4 kDa).

(2) Amino Acid Composition

The above-described polypeptide was hydrolyzed at 110° C. for 24 hr in 6N HCl and analyzed by a picotag system for amino acid analysis manufactured by Waters. Cysteine was quantitatively determined as cysteine by previously oxidizing the fungal PDI with performic acid and hydrolyzing the oxidation product with 6N HCl. The composition of the amino acid thus obtained is provided in Table 1.

TABLE 1

| Amino acid | Number of residues per molecule | |
| --- | --- | --- |
|  | Found | Calculated |
| Asp/Asn | 44.2 | 46 |
| Glu/Gln | 68.0 | 66 |
| His | 4.5 | 5 |
| Arg | 7.5 | 7 |
| Lys | 52.3 | 51 |
| Cys | 5.7 | 6 |
| Gly | 26.3 | 25 |
| Ser | 22.9 | 24 |
| Thr | 30.8 | 32 |
| Tyr | 18.7 | 17 |
| Ala | 61.4 | 63 |
| Val | 32.1 | 34 |
| Leu | 27.9 | 29 |
| Ile | 26.4 | 27 |
| Met | 1.7 | 2 |
| Phe | 28.0 | 26 |
| Pro | 25.1 | 23 |
| Trp | 1.8 | 2 |

The percentage of the amino acid composition was equivalent to a polypeptide possessing PDI activity produced by *Humicola insolens* KASI (FERM BP-4239).

Example 10: Properties of Polypeptide Possessing PDI Activity (a) Refolding of Sc-RNase Ribonuclease A (RNase) derived from bovine pancreas was scrambled for inactivation, and PDI activity was determined by refolding the inactivated RNase. Scrambling was effected according to a method described in Hillson, D. A., Lambert, N., Freedman, R. B., *Methods in Enzymology*, 107, 281–295, 1984. 5 μM Sc-RNase and 5 μM dithiothreitol were added in a 50 mM sodium phosphate buffer (pH 7.5) containing 1 mM ethylenediamine-tetraacetic acid (EDTA). 100 ng of the polypeptide possessing PDI activity was added thereto, and the volume of the mixture was adjusted to 50 μl. The mixture was incubated at 30° C. for 30 min. A 5 μl aliquot from the mixture was taken out each before and after the incubation and added to 495 μl of ribonucleic acid (0.1 mg/ml), and the amount of decomposition of the ribonucleic acid was measured by taking advantage of an increase in the absorbance at 260 nm to determine the RNase activity. The PDI activity was expressed in terms of the percentage increase in the absorbance per min. When use was made of the polypeptide possessing PDI activity protein provided in Example 2, 80% of Sc-RNase was activated by the above method.

(b) Refolding of Sc-Lysozyme

The PDI was allowed to act on an egg lysozyme and a bovine pancreas aprotinin each subjected to scrambling in the same manner as described above. As a result, as with the RNase, the activity of lysozyme and aprotinin were recovered.

Measurement of Lysozyme Activity

20 μl of an aqueous lysozyme solution was added to 80 μl of a 0.1M sodium acetate buffer (pH 5.5) containing 0.05% of ethylene glycol chitin, and the mixture was incubated at 40° C. for 30 min. Thereafter, 200 μl of 0.5 g/liter potassium ferricyanide (0.5M disodium carbonate solution) was added thereto, and the mixture was boiled for 15 min and cooled to room temperature, and the absorbance was measured at 420 nm.

Refolding of Sc-Lysozyme

7 μg of the PDI provided in Example 2 and 3 μg of Sc-lysozyme were dissolved in a 50 mM sodium phosphate buffer (1 mM EDTA added, pH 7.5) containing 5 μM dithiothreitol, and the volume of the mixture was adjusted to 20 μl. The mixture was incubated at 30° C. for one hr. Thereafter, the activity of the lysozyme subjected to refolding was measured. Under the above-described conditions, 12% of the Sc-lysozyme was reactivated.

(c) Reoxidation of Reduced Aprotinin with Polypeptide Possessing PDI Activity

The polypeptide possessing PDI activity provided in Example 2 was subjected to determination of the capability of oxidizing reduced aprotinin (bovine pancreatic trypsin inhibitor).

4 μg of the polypeptide possessing PDI activity and 1 μg of reduced aprotinin were dissolved in 100 μl of a 50 mM sodium phosphate buffer (1 mM EDTA added, pH 7.5) containing 5 μM dithiothreitol, and the mixture was incubated at 30° C. for one hour. The activity of the oxidized aprotinin was measured in terms of the trypsin inhibitory activity. Specifically, 2.5 μg of bovine trypsin dissolved in 70 μl of a 0.05M Tris-HCl buffer (0.02M calcium chloride added, pH 8.2) was added to the reaction mixture, the mixture was incubated at 37° C. for 15 min, the temperature was returned to 25° C., and 4.35 mg/ml benzoyl-L-arginine-P-nitroanilide (BAPA), which is a synthetic substrate for trypsin, and 30 μl of 0.05M Tris-HCl buffer (0.02M calcium chloride added, pH 8.2) are added to the mixture. Further, the mixture was incubated at 25° C. for 10 min, 50 μl of 30% acetic acid was added thereto to stop the reaction, and the absorbance was measured at 410 nm. Under the above-described conditions, 3% of the reduced aprotinin was oxidized.

(d) Thermostability

Figure 4:
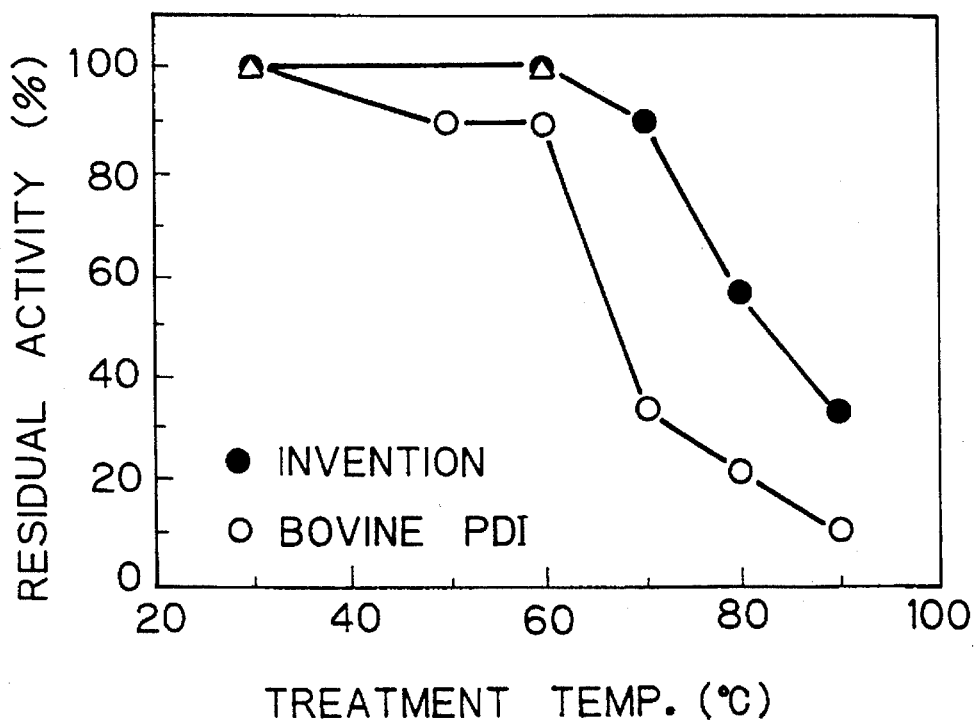
FIG. 4 is a graph showing the thermostability of a polypeptide possessing PDI activity prepared in Example 2.

The polypeptide possessing PDI activity provided in Example 2 and bovine PDI were heated at 30° to 90° C. for 30 min in a phosphate buffer (pH 7.5), and the residual PDI activity was measured. The results are shown in FIG. 4. In FIG. 4, the activity of the PDI not heated was expressed as 100%. As is apparent from FIG. 4, the polypeptide possessing PDI activity of the present invention was superior in the thermostability to the bovine PDI.

(e) Temperature Dependency

Figure 5:
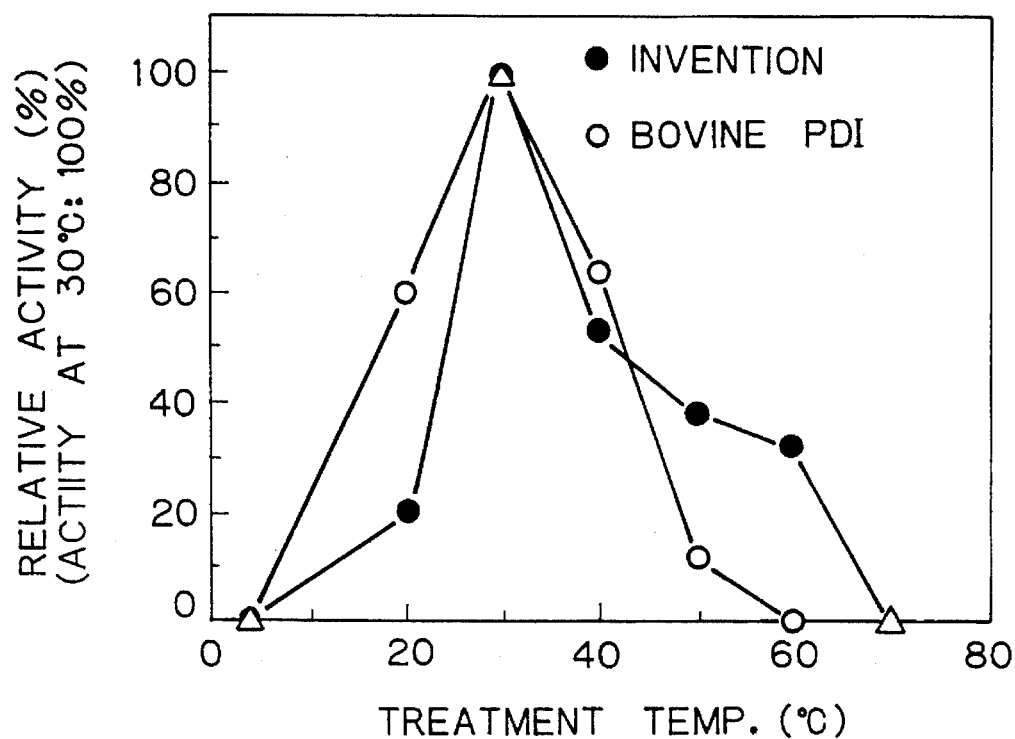
FIG. 5 is a graph showing the temperature dependency of the activity in a refolding reaction of a polypeptide possessing PDI activity prepared in Example 2.

The temperature dependency of the refolding reaction of the polypeptide possessing PDI activity provided in Example 2 and bovine PDI was determined by using Sc-RNase. The results are shown in FIG. 5. In each case, the activity in the reaction at 30° C. was taken as 100%.

As is apparent from FIG. 5, the polypeptide possessing PDI activity of the present invention was superior to the bovine PDI in a reactivity at temperatures of 50° C. or above.

(f) pH Stability

Figure 6:
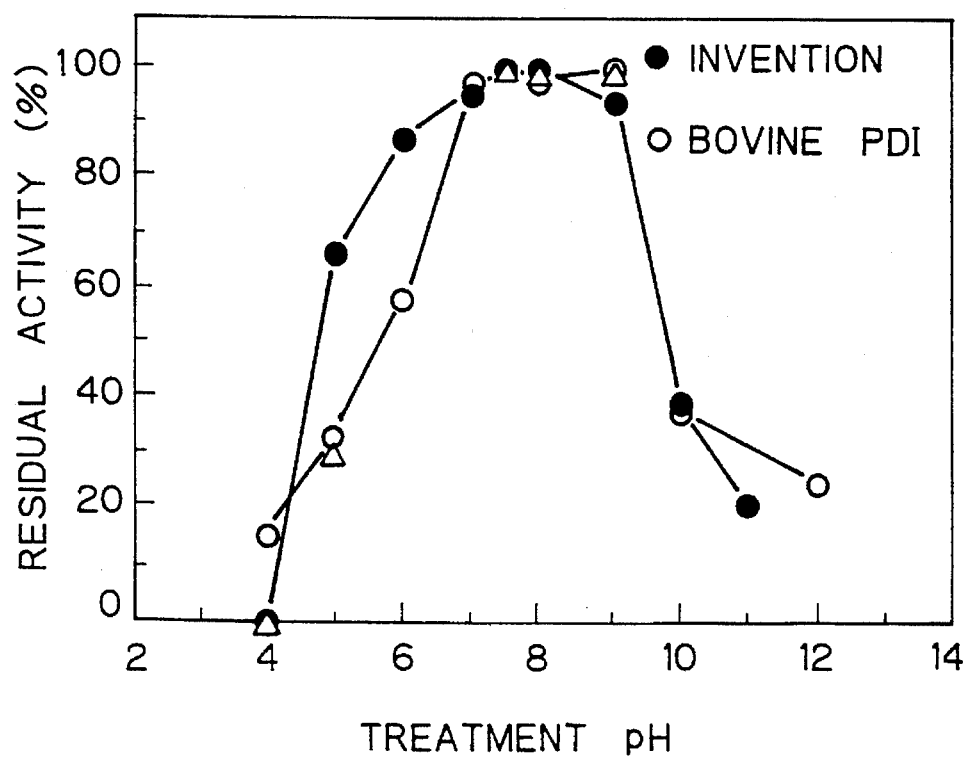
FIG. 6 is a graph showing the pH stability of a polypeptide possessing PDI activity prepared in Example 2.

The polypeptide possessing PDI activity provided in Example 2 and bovine PDI were allowed to stand in Britton-Robinson's buffer (pH: 4 to 12) at 30° C. for 30 min, and the residual activity was then measured. The activity of each PDI stored at pH 7.5 and 4° C. was taken as 100%. The results are provided in FIG. 6. As is apparent from FIG. 6, the polypeptide possessing PDI activity of the present invention exhibited a tendency that the stability was slightly higher than that of the bovine PDI on the acidic side.

(g) pH Dependency

Figure 7:
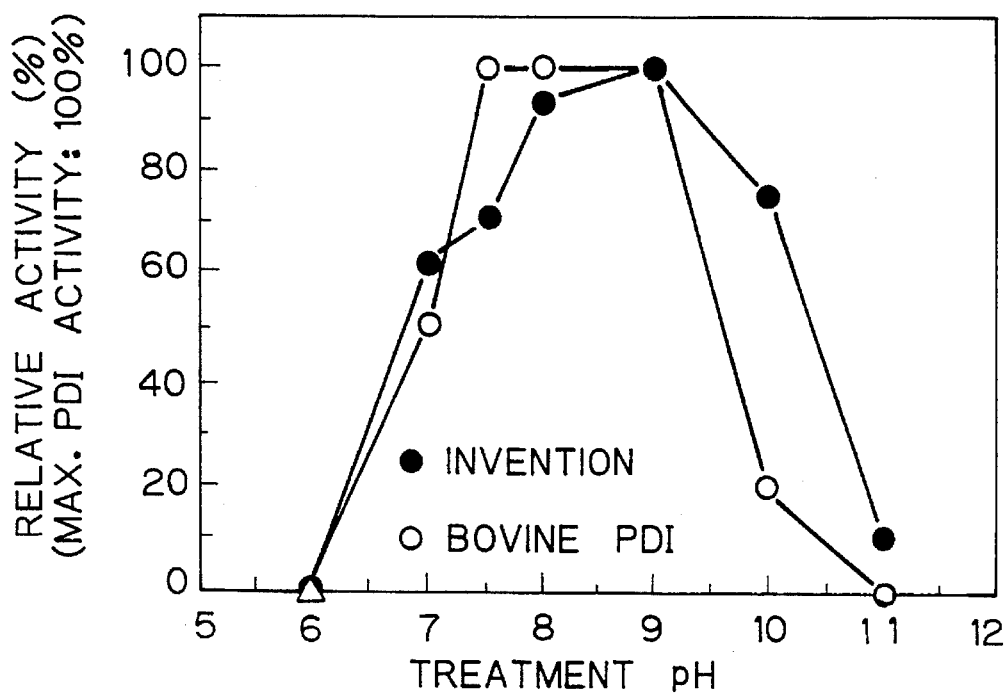
FIG. 7 is a graph showing the pH dependency of the activity in a refolding reaction of a polypeptide possessing PDI activity prepared in Example 2.

The activity of the polypeptide possessing PDI activity provided in Example 2 and bovine PDI was examined using Sc-RNase with the pH value being varied during refolding. In each case, since the activity was maximum at pH 9, the activity was expressed in terms of the relative activity assuming that the activity at pH 9 was 100%. The results are shown in FIG. 7. The polypeptide possessing PDI activity of the present invention exhibited a tendency that the activity against the SC-RNase was higher than that of the bovine PDI on the alkaline side and slightly lower than that of the bovine PDI on the acidic side.

(h) Influence of Dithiothreitol

Figure 8:
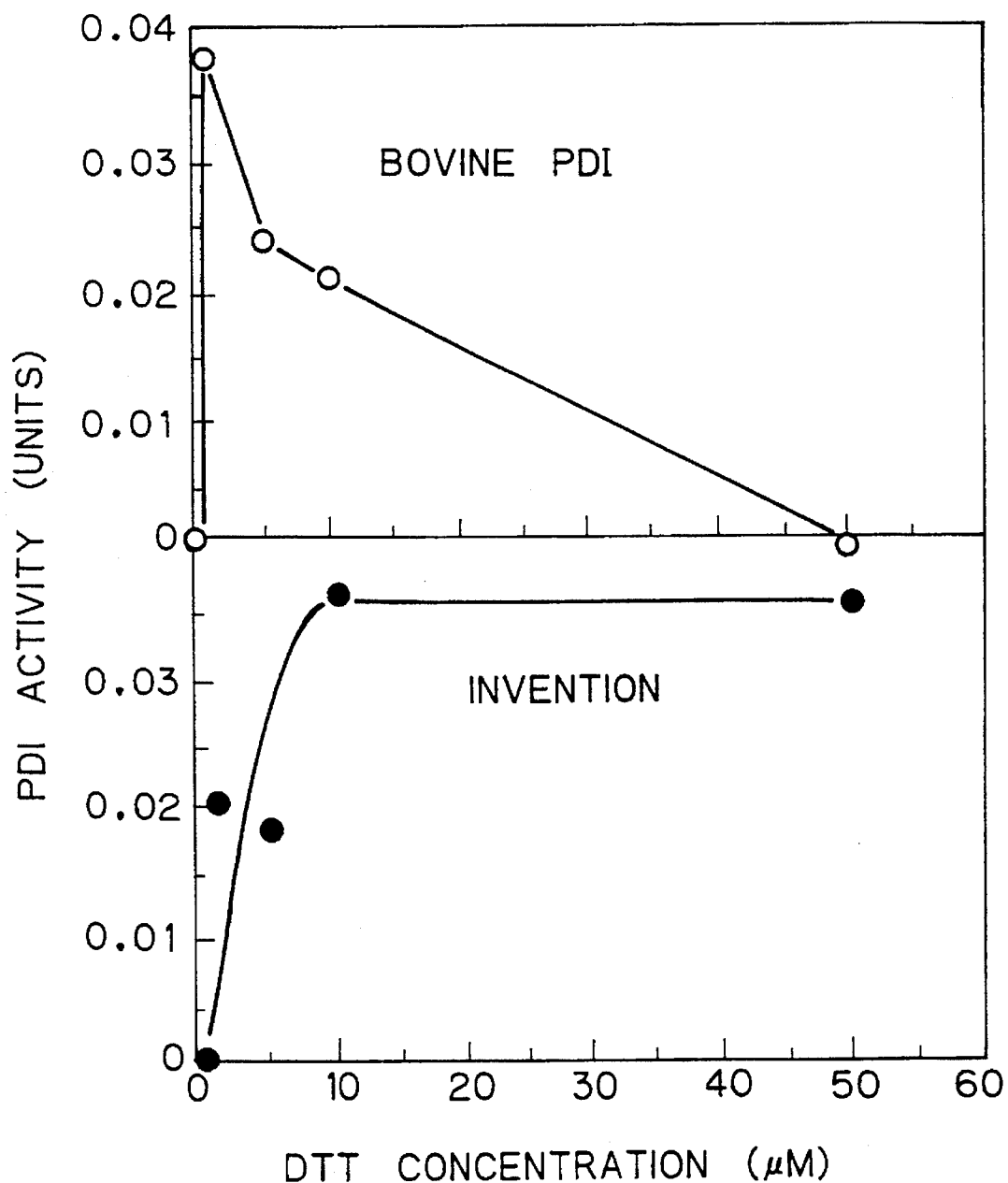
FIG. 8 is a graph showing the effect of the DTT concentration on the activity in a refolding reaction of a polypeptide possessing PDI activity prepared in Example 2.

When PDI is used in a refolding reaction, it is necessary to add an SH reducing agent, such as dithiothreitol or reduced glutathione. Accordingly, the change of the activity of 40 ng of each of the polypeptide possessing PDI activity provided in Example 2 and bovine PDI with the concentration of dithiothreitol (DTT) was determined, and the results are shown in FIG. 8. The activity was expressed in terms of the relative activity by taking the maximum activity as 100%. As is apparent from FIG. 8, the bovine PDI had an optimum DTT concentration of 1 mM, and the activity lowered with increasing the concentration of DTT, whereas the polypeptide possessing PDI activity of the present invention exhibited a stable activity in a wide DTT concentration range of from 1 to 50 mM.

(i) Influence of Bacitracin

It is known that bovine PDI and yeast PDI are inhibited by bacitracin which is an antibiotic derived from *Bacillus subtilis* (see Mizunaga, T., Kitakura, Y., Miura, T., Marugama, Y. *Journal of Biochemistry*, 108, 846–851, (1990)).

Figure 9:
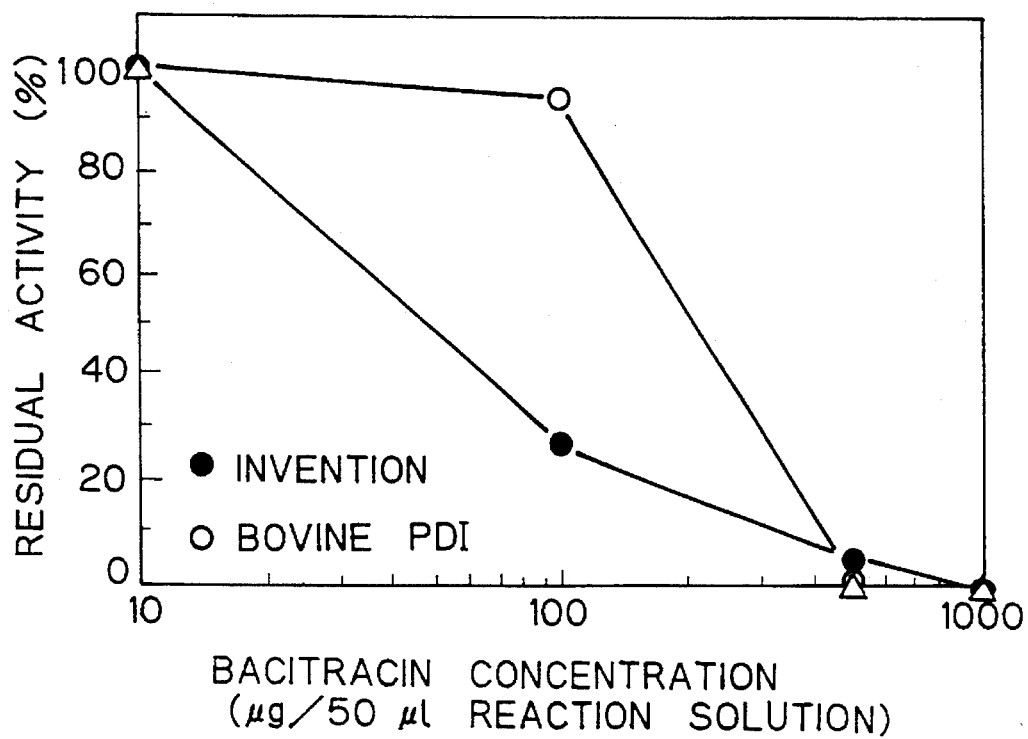
FIG. 9 is a graph showing the influence of bacitracin on the activity in a refolding reaction of a polypeptide possessing PDI activity prepared in Example 2.

Accordingly, the influence of bacitracin on the activity was determined also for the polypeptide possessing PDI activity provided in Example 2. The results are shown in FIG. 9. As is apparent from FIG. 9, the polypeptide possessing PDI activity of the present invention had a higher susceptibility to bacitracin than the bovine PDI.

(j) Long-Term Stability at Room Temperature

Figure 10:
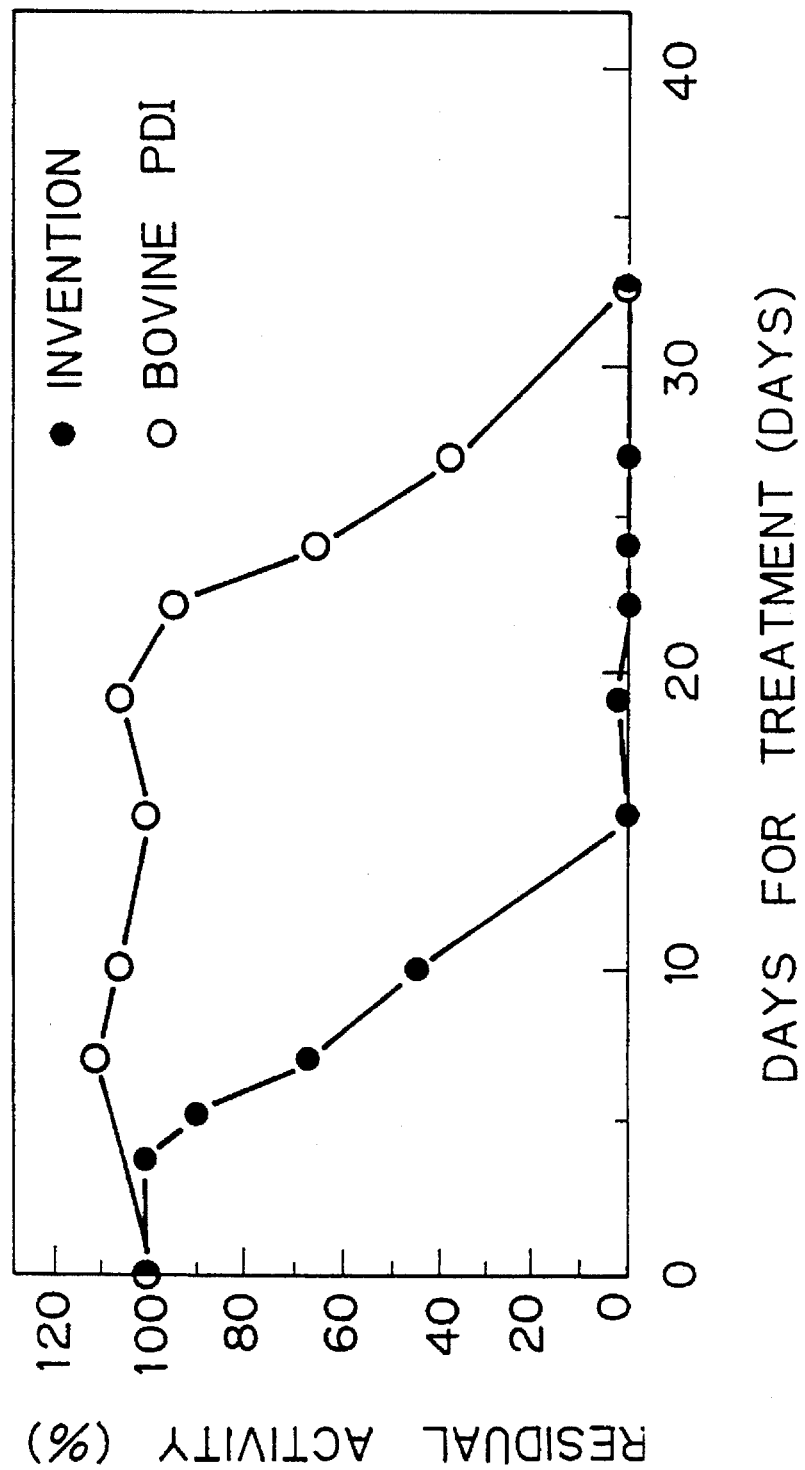
FIG. 10 is a graph showing the long-term stability at room temperature of a polypeptide possessing PDI activity prepared in Example 2 in comparison with that of bovine PDI.

The polypeptide possessing PDI activity provided in Example 2 and bovine PDI were allowed to stand in a 50 mM phosphate buffer (pH 7.5) containing 1 mM EDTA and 0.01% sodium azide at room temperature for 33 days. During this period, the PDI activity was measured at suitable intervals to determine the long-term stability. The results are shown in FIG. 10. In FIG. 10, the activity on the first day was expressed as 100%. As is apparent from the results, the number of days showing 90% or more of the activity on the first day was 3 days for the bovine PDI, whereas it was 20 days or more for the polypeptide possessing PDI activity of the present invention. Further, the bovine PDI completely lost its activity in 15 days. By contrast, the polypeptide possessing PDI activity of the present invention remained active over 30 days or longer. Thus, it was found that the polypeptide possessing PDI activity of the present invention was superior to the bovine PDI in the long-term stability at room temperature.

Example 11: Properties of Recombinant PDI

The properties of polypeptide possessing PDI activity obtained in Example 8 were compared with those of the polypeptide obtained in Example 2. The results are shown in Table 2.

TABLE 2

| Comparison Items | Example 2 | Example 8 |
|---|---|---|
| Molecular weight | 60,000–62,000 | 60,000–61,000 |
| Refolding Ratio of Sc-RNase (%) | 80 | 82 |
| Thermostability (70° C., 30 min.) | Residual activity >90% | >90% |
| pH Stability (pH 6–9, 30° C., 30 min.) | Residual activity >80% | >85% |
| Long-Term Stability (room temp., 20 days) | Residual activity >90% | >95% |
| Influence of DTT (1–50 mM) | Active | Active |
| Influence of Guanidine Hydrochloride | Active | Active |

In Table 2, the molecular weights, the refolding ratios of Sc-RNase, the thermostabilities, the pH stabilities, the long-term stabilities, and the influences of DTT were determined as described in Example 9, Example 10(a), Example 10(d), Example 10(f), Example 10(j), and Example 10(h), respectively. With respect to the influences of guanidine hydrochloride, tests were conducted under the conditions as described in Example 10(a) except for using 0.2M guanidine hydrochloride, as to whether or not there was PDI activity. As shown in Table 2, both polypeptides possessing PDI activity have the same properties.

We claim:

1. An isolated thermostable polypeptide of *Humicola insolens* KASI origin, possessing protein disulfide isomerase activity which catalyses a disulfide exchange in protein, and being characterized by the following properties:

A) it carries out disulfide exchange at least on ribonuclease A;

B) a suitable temperature for the enzyme to be active is 20° to 70° C.;

C) its residual activity after a treatment for 30 minutes at pH 7.5 is about 100% at a temperature between 30° C. and 60° C., more than 80% at a temperature of 70° C., and more than 50% at a temperature of 80° C., taking the activity before said treatment as 100%;

D) it is stable at a pH value of 6 to 9;

E) its residual activity after a treatment for 30 minutes at 30° C. is more than 60% at pH 5, more than 80% at pH 6, more than 90% at pH of from 8 to 9, and more than 30% at pH 10, taking the activity before said treatment as 100%; and F) it has a molecular weight of about 60,000 to 62,000, as measured by SDS-polyacrylamide gel electrophoresis.

2. The polypeptide of claim 1, having the sequence of SEQ ID NO:1.

\* \* \* \* \*

UNITED STATES PATENT AND TRADEMARK OFFICE
CERTIFICATE OF CORRECTION

PATENT NO.  :   5,496,719
DATED:      :   March 5, 1996
INVENTOR(S) :   Yukio YAMADA et al It is certified that error appears in the above-identified patent and that said Letters patent is hereby corrected as shown below:

In the Drawings, Fig. 10, in the Legend,

" ● INVENTION

○ BOVINE PDI"     should read

-- ● BOVINE PDI

○ INVENTION --.

Signed and Sealed this

First Day of September, 1998

Attest:

BRUCE LEHMAN

Attesting Officer          Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 485 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ser  Asp  Val  Val  Gln  Leu  Lys  Lys  Asp  Thr  Phe  Asp  Asp  Phe  Ile  Lys
  1              5                    10                           15

Thr  Asn  Asp  Leu  Val  Leu  Ala  Glu  Phe  Phe  Ala  Pro  Trp  Cys  Gly  His
               20                   25                      30

Cys  Lys  Ala  Leu  Ala  Pro  Glu  Tyr  Glu  Glu  Ala  Ala  Thr  Thr  Leu  Lys
          35                        40                      45

Glu  Lys  Asn  Ile  Lys  Leu  Ala  Lys  Val  Asp  Cys  Thr  Glu  Glu  Thr  Asp
     50                   55                   60

Leu  Cys  Gln  Gln  His  Gly  Val  Glu  Gly  Tyr  Pro  Thr  Leu  Lys  Val  Phe
 65                       70                   75                           80

Arg  Gly  Leu  Asp  Asn  Val  Ser  Pro  Tyr  Lys  Gly  Gln  Arg  Lys  Ala  Ala
               85                        90                           95

Ala  Ile  Thr  Ser  Tyr  Met  Ile  Lys  Gln  Ser  Leu  Pro  Ala  Val  Ser  Glu
              100                       105                     110

Val  Thr  Lys  Asp  Asn  Leu  Glu  Glu  Phe  Lys  Lys  Ala  Asp  Lys  Ala  Val
          115                       120                     125

Leu  Val  Ala  Tyr  Val  Asp  Ala  Ser  Asp  Lys  Ala  Ser  Ser  Glu  Val  Phe
     130                      135                     140

Thr  Gln  Val  Ala  Glu  Lys  Leu  Arg  Asp  Asn  Tyr  Pro  Phe  Gly  Ser  Ser
145                       150                      155                     160

Ser  Asp  Ala  Ala  Leu  Ala  Glu  Ala  Glu  Gly  Val  Lys  Ala  Pro  Ala  Ile
                    165                      170                     175

Val  Leu  Tyr  Lys  Asp  Phe  Asp  Glu  Gly  Lys  Ala  Val  Phe  Ser  Glu  Lys
               180                      185                     190

Phe  Glu  Val  Glu  Ala  Ile  Glu  Lys  Phe  Ala  Lys  Thr  Gly  Ala  Thr  Pro
          195                      200                     205

Leu  Ile  Gly  Glu  Ile  Gly  Pro  Glu  Thr  Tyr  Ser  Asp  Tyr  Met  Ser  Ala
     210                      215                     220

Gly  Ile  Pro  Leu  Ala  Tyr  Ile  Phe  Ala  Glu  Thr  Ala  Glu  Glu  Arg  Lys
225                       230                      235                     240

Glu  Leu  Ser  Asp  Lys  Leu  Lys  Pro  Ile  Ala  Glu  Ala  Gln  Arg  Gly  Val
                    245                      250                     255

Ile  Asn  Phe  Gly  Thr  Ile  Asp  Ala  Lys  Ala  Phe  Gly  Ala  His  Ala  Gly
               260                      265                     270

Asn  Leu  Asn  Leu  Lys  Thr  Asp  Lys  Phe  Pro  Ala  Phe  Ala  Ile  Gln  Glu
          275                      280                     285

Val  Ala  Lys  Asn  Gln  Lys  Phe  Pro  Phe  Asp  Gln  Glu  Lys  Glu  Ile  Thr
     290                      295                     300

Phe  Glu  Ala  Ile  Lys  Ala  Phe  Val  Asp  Asp  Phe  Val  Ala  Gly  Lys  Ile
305                       310                      315                     320

Glu  Pro  Ser  Ile  Lys  Ser  Glu  Pro  Ile  Pro  Glu  Lys  Gln  Glu  Gly  Pro
```

|  |  |  |  |  | 325 |  |  |  | 330 |  |  |  | 335 |  |
|---|---|---|---|---|---|---|---|---|---|---|---|---|---|---|
| Val | Thr | Val | Val | Val | Ala | Lys | Asn | Tyr | Asn | Glu | Ile | Val | Leu | Asp | Asp |
|  |  |  | 340 |  |  |  |  | 345 |  |  |  | 350 |  |  |
| Thr | Lys | Asp | Val | Leu | Ile | Glu | Phe | Tyr | Ala | Pro | Trp | Cys | Gly | His | Cys |
|  |  | 355 |  |  |  |  | 360 |  |  |  |  | 365 |  |  |
| Lys | Ala | Leu | Ala | Pro | Lys | Tyr | Glu | Glu | Leu | Gly | Ala | Leu | Tyr | Ala | Lys |
|  | 370 |  |  |  |  | 375 |  |  |  |  | 380 |  |  |  |
| Ser | Glu | Phe | Lys | Asp | Arg | Val | Val | Ile | Ala | Lys | Val | Asp | Ala | Thr | Ala |
| 385 |  |  |  |  | 390 |  |  |  |  | 395 |  |  |  |  | 400 |
| Asn | Asp | Val | Pro | Asp | Glu | Ile | Gln | Gly | Phe | Pro | Thr | Ile | Lys | Leu | Tyr |
|  |  |  |  | 405 |  |  |  |  | 410 |  |  |  |  | 415 |  |
| Pro | Ala | Gly | Ala | Lys | Gly | Gln | Pro | Val | Thr | Tyr | Ser | Gly | Ser | Arg | Thr |
|  |  |  | 420 |  |  |  |  | 425 |  |  |  |  | 430 |  |  |
| Val | Glu | Asp | Leu | Ile | Lys | Phe | Ile | Ala | Glu | Asn | Gly | Lys | Tyr | Lys | Ala |
|  |  | 435 |  |  |  |  | 440 |  |  |  |  | 445 |  |  |  |
| Ala | Ile | Ser | Glu | Asp | Ala | Glu | Glu | Thr | Ser | Ser | Ala | Thr | Glu | Thr | Thr |
|  | 450 |  |  |  |  | 455 |  |  |  |  | 460 |  |  |  |  |
| Thr | Glu | Thr | Ala | Thr | Lys | Ser | Glu | Glu | Ala | Ala | Lys | Glu | Thr | Ala | Thr |
| 465 |  |  |  |  | 470 |  |  |  |  | 475 |  |  |  |  | 480 |
| Glu | His | Asp | Glu | Leu |  |  |  |  |  |  |  |  |  |  |  |
|  |  |  |  | 485 |  |  |  |  |  |  |  |  |  |  |  |

( 2 ) INFORMATION FOR SEQ ID NO:2:

( i ) SEQUENCE CHARACTERISTICS:
        ( A ) LENGTH: 1755 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Humicola insolens ( i x ) FEATURE:
        ( A ) NAME/KEY: CDS
        ( B ) LOCATION: 110..1624

( i x ) FEATURE:
        ( A ) NAME/KEY: sig_peptide
        ( B ) LOCATION: 110..169

( i x ) FEATURE:
        ( A ) NAME/KEY: mat_peptide
        ( B ) LOCATION: 170..1624

( x i ) SEQUENCE DESCRIPTION: SEQ ID NO:2:

```
CGCATACCTG CAGGGTATCA ATTGGAATTC AATTCCTTGG TTGCGGTGAT TCCTCCTATC          60

TGTCCTTTTC TGCCTTTACT TTAAGTAGCC CAGAAACAGG AACATCGCG ATG CAT           115
                                                     Met His
                                                      -20

AAG GCC CAG AAG TTC GCG CTC GGC CTC CTT GCC GCG GCG GCA GTT GCC         163
Lys Ala Gln Lys Phe Ala Leu Gly Leu Leu Ala Ala Ala Ala Val Ala
              -15                 -10                  -5

ACA GCT TCG GAT GTT GTC CAG CTG AAG AAG GAC ACC TTC GAC GAC TTC         211
Thr Ala Ser Asp Val Val Gln Leu Lys Lys Asp Thr Phe Asp Asp Phe
             1               5                  10

ATC AAG ACG AAT GAC CTT GTT CTC GCC GAA TTC TTC GCG CCG TGG TGC         259
Ile Lys Thr Asn Asp Leu Val Leu Ala Glu Phe Phe Ala Pro Trp Cys
 15               20                 25                     30

GGT CAC TGC AAG GCT CTC GCC CCC GAG TAC GAG GAG GCT GCG ACC ACA         307
Gly His Cys Lys Ala Leu Ala Pro Glu Tyr Glu Glu Ala Ala Thr Thr
```

|   |   |   |   |   | 35 |   |   |   |   | 40 |   |   |   |   | 45 |   |   |
|---|---|---|---|---|---|---|---|---|---|---|---|---|---|---|---|---|---|

```
CTG AAG GAG AAG AAC ATC AAG CTC GCC AAG GTG GAC TGC ACA GAG GAG      355
Leu Lys Glu Lys Asn Ile Lys Leu Ala Lys Val Asp Cys Thr Glu Glu
         50                  55                  60

ACG GAC CTC TGC CAA CAA CAT GGT GTT GAG GGC TAC CCG ACT CTC AAG      403
Thr Asp Leu Cys Gln Gln His Gly Val Glu Gly Tyr Pro Thr Leu Lys
         65                  70                  75

GTC TTC CGC GGC CTT GAC AAC GTC TCC CCC TAC AAG GGC CAG CGC AAG      451
Val Phe Arg Gly Leu Asp Asn Val Ser Pro Tyr Lys Gly Gln Arg Lys
         80                  85                  90

GCT GCT GCT ATC ACC TCG TAC ATG ATC AAG CAG TCT CTG CCC GCC GTG      499
Ala Ala Ala Ile Thr Ser Tyr Met Ile Lys Gln Ser Leu Pro Ala Val
95                  100                 105                 110

TCC GAG GTC ACG AAG GAC AAC CTG GAG GAG TTC AAG AAG GCC GAC AAG      547
Ser Glu Val Thr Lys Asp Asn Leu Glu Glu Phe Lys Lys Ala Asp Lys
                115                 120                 125

GCC GTC CTT GTC GCC TAT GTG GAT GCT TCC GAC AAG GCG TCC AGT GAG      595
Ala Val Leu Val Ala Tyr Val Asp Ala Ser Asp Lys Ala Ser Ser Glu
                130                 135                 140

GTT TTC ACC CAG GTC GCC GAG AAG CTG CGC GAC AAC TAC CCG TTC GGC      643
Val Phe Thr Gln Val Ala Glu Lys Leu Arg Asp Asn Tyr Pro Phe Gly
        145                 150                 155

TCC AGC AGC GAT GCT GCG CTG GCC GAG GCT GAG GGC GTC AAG GCT CCC      691
Ser Ser Ser Asp Ala Ala Leu Ala Glu Ala Glu Gly Val Lys Ala Pro
160                 165                 170

GCT ATC GTC CTT TAC AAG GAC TTT GAT GAG GGC AAG GCG GTC TTC TCC      739
Ala Ile Val Leu Tyr Lys Asp Phe Asp Glu Gly Lys Ala Val Phe Ser
175                 180                 185                 190

GAG AAG TTC GAG GTG GAG GCG ATC GAG AAG TTC GCC AAG ACG GGC GCC      787
Glu Lys Phe Glu Val Glu Ala Ile Glu Lys Phe Ala Lys Thr Gly Ala
                195                 200                 205

ACC CCG CTC ATT GGC GAG ATT GGC CCC GAA ACC TAC TCC GAC TAC ATG      835
Thr Pro Leu Ile Gly Glu Ile Gly Pro Glu Thr Tyr Ser Asp Tyr Met
            210                 215                 220

TCG GCC GGC ATC CCT CTG GCC TAC ATT TTC GCC GAA ACG GCC GAG GAG      883
Ser Ala Gly Ile Pro Leu Ala Tyr Ile Phe Ala Glu Thr Ala Glu Glu
        225                 230                 235

CGG AAG GAG CTC AGC GAC AAG CTC AAG CCG ATC GCC GAG GCT CAG CGC      931
Arg Lys Glu Leu Ser Asp Lys Leu Lys Pro Ile Ala Glu Ala Gln Arg
        240                 245                 250

GGC GTC ATT AAC TTT GGT ACT ATT GAC GCC AAG GCT TTT GGT GCC CAC      979
Gly Val Ile Asn Phe Gly Thr Ile Asp Ala Lys Ala Phe Gly Ala His
255                 260                 265                 270

GCC GGC AAC CTG AAC CTG AAG ACC GAC AAG TTC CCC GCC TTC GCC ATC     1027
Ala Gly Asn Leu Asn Leu Lys Thr Asp Lys Phe Pro Ala Phe Ala Ile
                275                 280                 285

CAG GAG GTC GCC AAG AAC CAG AAG TTC CCC TTC GAT CAG GAG AAG GAG     1075
Gln Glu Val Ala Lys Asn Gln Lys Phe Pro Phe Asp Gln Glu Lys Glu
                290                 295                 300

ATC ACC TTC GAG GCG ATC AAG GCT TTC GTC GAC GAC TTT GTC GCC GGT     1123
Ile Thr Phe Glu Ala Ile Lys Ala Phe Val Asp Asp Phe Val Ala Gly
        305                 310                 315

AAG ATC GAG CCC AGC ATC AAG TCG GAG CCG ATC CCT GAG AAG CAG GAG     1171
Lys Ile Glu Pro Ser Ile Lys Ser Glu Pro Ile Pro Glu Lys Gln Glu
        320                 325                 330

GGC CCC GTC ACC GTC GTC GTT GCC AAG AAC TAC AAT GAG ATC GTC CTG     1219
Gly Pro Val Thr Val Val Val Ala Lys Asn Tyr Asn Glu Ile Val Leu
335                 340                 345                 350

GAC GAC ACC AAG GAT GTG CTG ATT GAG TTC TAC GCC CCG TGG TGC GGC     1267
Asp Asp Thr Lys Asp Val Leu Ile Glu Phe Tyr Ala Pro Trp Cys Gly
```

|  |  |  |  |  |  | 355 |  |  |  |  | 360 |  |  |  |  | 365 |  |  |
|---|---|---|---|---|---|---|---|---|---|---|---|---|---|---|---|---|---|---|

```
CAC  TGC  AAG  GCC  CTG  GCT  CCC  AAG  TAC  GAG  GAG  CTC  GGC  GCC  CTG  TAT        1315
His  Cys  Lys  Ala  Leu  Ala  Pro  Lys  Tyr  Glu  Glu  Leu  Gly  Ala  Leu  Tyr
               370                      375                      380

GCC  AAG  AGC  GAG  TTC  AAG  GAC  CGG  GTC  GTC  ATC  GCC  AAG  GTT  GAT  GCC        1363
Ala  Lys  Ser  Glu  Phe  Lys  Asp  Arg  Val  Val  Ile  Ala  Lys  Val  Asp  Ala
               385                      390                      395

ACG  GCC  AAC  GAC  GTT  CCC  GAT  GAG  ATC  CAG  GGA  TTC  CCC  ACC  ATC  AAG        1411
Thr  Ala  Asn  Asp  Val  Pro  Asp  Glu  Ile  Gln  Gly  Phe  Pro  Thr  Ile  Lys
     400                      405                      410

CTG  TAC  CCG  GCC  GGT  GCC  AAG  GGT  CAG  CCC  GTC  ACC  TAC  TCT  GGC  TCG        1459
Leu  Tyr  Pro  Ala  Gly  Ala  Lys  Gly  Gln  Pro  Val  Thr  Tyr  Ser  Gly  Ser
415                      420                      425                      430

CGC  ACT  GTC  GAG  GAC  CTC  ATC  AAG  TTC  ATC  GCC  GAG  AAC  GGC  AAG  TAC        1507
Arg  Thr  Val  Glu  Asp  Leu  Ile  Lys  Phe  Ile  Ala  Glu  Asn  Gly  Lys  Tyr
               435                      440                      445

AAG  GCC  GCC  ATC  TCG  GAG  GAT  GCC  GAG  GAG  ACG  TCG  TCC  GCA  ACC  GAG        1555
Lys  Ala  Ala  Ile  Ser  Glu  Asp  Ala  Glu  Glu  Thr  Ser  Ser  Ala  Thr  Glu
               450                      455                      460

ACG  ACC  ACC  GAG  ACG  GCC  ACC  AAG  TCG  GAG  GAG  GCT  GCC  AAG  GAG  ACG        1603
Thr  Thr  Thr  Glu  Thr  Ala  Thr  Lys  Ser  Glu  Glu  Ala  Ala  Lys  Glu  Thr
          465                      470                      475

GCG  ACG  GAG  CAC  GAC  GAG  CTC  TAGAAGACTT  GTCGTACATG  TATTTTACGA                 1654
Ala  Thr  Glu  His  Asp  Glu  Leu
          480                485

AATGCTTTCT  TGGGTTTTTC  ATTAGGGACC  ATAGGCACGC  GGATCCAGGG  GCCCGGTATT               1714

CTTGGGATTG  GGTTTTGCCA  AAATACCACC  GCGCATCTAT  G                                    1755
```

( 2 ) INFORMATION FOR SEQ ID NO:3:

( i ) SEQUENCE CHARACTERISTICS:
        ( A ) LENGTH: 505 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  His  Lys  Ala  Gln  Lys  Phe  Ala  Leu  Gly  Leu  Leu  Ala  Ala  Ala  Ala
-20                 -15                      -10                           -5

Val  Ala  Thr  Ala  Ser  Asp  Val  Val  Gln  Leu  Lys  Lys  Asp  Thr  Phe  Asp
               1                        5                        10

Asp  Phe  Ile  Lys  Thr  Asn  Asp  Leu  Val  Leu  Ala  Glu  Phe  Phe  Ala  Pro
          15                       20                       25

Trp  Cys  Gly  His  Cys  Lys  Ala  Leu  Ala  Pro  Glu  Tyr  Glu  Glu  Ala  Ala
     30                       35                       40

Thr  Thr  Leu  Lys  Glu  Lys  Asn  Ile  Lys  Leu  Ala  Lys  Val  Asp  Cys  Thr
45                       50                       55                       60

Glu  Glu  Thr  Asp  Leu  Cys  Gln  Gln  His  Gly  Val  Glu  Gly  Tyr  Pro  Thr
                    65                       70                       75

Leu  Lys  Val  Phe  Arg  Gly  Leu  Asp  Asn  Val  Ser  Pro  Tyr  Lys  Gly  Gln
               80                       85                       90

Arg  Lys  Ala  Ala  Ala  Ile  Thr  Ser  Tyr  Met  Ile  Lys  Gln  Ser  Leu  Pro
          95                       100                      105

Ala  Val  Ser  Glu  Val  Thr  Lys  Asp  Asn  Leu  Glu  Glu  Phe  Lys  Lys  Ala
          110                      115                      120

Asp  Lys  Ala  Val  Leu  Val  Ala  Tyr  Val  Asp  Ala  Ser  Asp  Lys  Ala  Ser
125                      130                      135                      140
```

```
Ser  Glu  Val  Phe  Thr  Gln  Val  Ala  Glu  Lys  Leu  Arg  Asp  Asn  Tyr  Pro
               145            150                      155

Phe  Gly  Ser  Ser  Ser  Asp  Ala  Ala  Leu  Ala  Glu  Ala  Glu  Gly  Val  Lys
               160                 165                      170

Ala  Pro  Ala  Ile  Val  Leu  Tyr  Lys  Asp  Phe  Asp  Glu  Gly  Lys  Ala  Val
          175                      180                 185

Phe  Ser  Glu  Lys  Phe  Glu  Val  Glu  Ala  Ile  Glu  Lys  Phe  Ala  Lys  Thr
     190                      195                 200

Gly  Ala  Thr  Pro  Leu  Ile  Gly  Glu  Ile  Gly  Pro  Glu  Thr  Tyr  Ser  Asp
205                      210                 215                           220

Tyr  Met  Ser  Ala  Gly  Ile  Pro  Leu  Ala  Tyr  Ile  Phe  Ala  Glu  Thr  Ala
               225                      230                      235

Glu  Glu  Arg  Lys  Glu  Leu  Ser  Asp  Lys  Leu  Lys  Pro  Ile  Ala  Glu  Ala
               240                 245                      250

Gln  Arg  Gly  Val  Ile  Asn  Phe  Gly  Thr  Ile  Asp  Ala  Lys  Ala  Phe  Gly
          255                 260                      265

Ala  His  Ala  Gly  Asn  Leu  Asn  Leu  Lys  Thr  Asp  Lys  Phe  Pro  Ala  Phe
     270                 275                      280

Ala  Ile  Gln  Glu  Val  Ala  Lys  Asn  Gln  Lys  Phe  Pro  Phe  Asp  Gln  Glu
285                      290                 295                           300

Lys  Glu  Ile  Thr  Phe  Glu  Ala  Ile  Lys  Ala  Phe  Val  Asp  Asp  Phe  Val
               305                      310                      315

Ala  Gly  Lys  Ile  Glu  Pro  Ser  Ile  Lys  Ser  Glu  Pro  Ile  Pro  Glu  Lys
               320                 325                      330

Gln  Glu  Gly  Pro  Val  Thr  Val  Val  Ala  Lys  Asn  Tyr  Asn  Glu  Ile
          335                 340                      345

Val  Leu  Asp  Asp  Thr  Lys  Asp  Val  Leu  Ile  Glu  Phe  Tyr  Ala  Pro  Trp
     350                      355                      360

Cys  Gly  His  Cys  Lys  Ala  Leu  Ala  Pro  Lys  Tyr  Glu  Glu  Leu  Gly  Ala
365                      370                 375                           380

Leu  Tyr  Ala  Lys  Ser  Glu  Phe  Lys  Asp  Arg  Val  Val  Ile  Ala  Lys  Val
               385                      390                      395

Asp  Ala  Thr  Ala  Asn  Asp  Val  Pro  Asp  Glu  Ile  Gln  Gly  Phe  Pro  Thr
          400                      405                      410

Ile  Lys  Leu  Tyr  Pro  Ala  Gly  Ala  Lys  Gly  Gln  Pro  Val  Thr  Tyr  Ser
          415                      420                 425

Gly  Ser  Arg  Thr  Val  Glu  Asp  Leu  Ile  Lys  Phe  Ile  Ala  Glu  Asn  Gly
     430                      435                 440

Lys  Tyr  Lys  Ala  Ala  Ile  Ser  Glu  Asp  Ala  Glu  Glu  Thr  Ser  Ser  Ala
445                      450                      455                      460

Thr  Glu  Thr  Thr  Thr  Glu  Thr  Ala  Thr  Lys  Ser  Glu  Glu  Ala  Ala  Lys
               465                      470                      475

Glu  Thr  Ala  Thr  Glu  His  Asp  Glu  Leu
               480                 485
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Trp  Cys  Gly  His  Cys  Lys
 1                  5
```

( 2 ) INFORMATION FOR SEQ ID NO:5:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

Lys  Asp  Thr  Phe  Asp  Asp  Phe  Ile
1                   5

( 2 ) INFORMATION FOR SEQ ID NO:6:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

Glu  Val  Gly  His  Gln  Gln  Cys
1                   5

( 2 ) INFORMATION FOR SEQ ID NO:7:

( i ) SEQUENCE CHARACTERISTICS:
    ( A ) LENGTH: 31 base pairs
    ( B ) TYPE: nucleic acid
    ( C ) STRANDEDNESS: unknown
    ( D ) TOPOLOGY: linear ( i i ) MOLECULE TYPE: Other nucleic acid;
    ( A ) DESCRIPTION: synthetic DNA ( x i ) SEQUENCE DESCRIPTION: SEQ ID NO:7:

GGGAATTCAA RGAYACNTTY GAYGAYTTYA T                                       31

( 2 ) INFORMATION FOR SEQ ID NO:8:

( i ) SEQUENCE CHARACTERISTICS:
    ( A ) LENGTH: 28 base pairs
    ( B ) TYPE: nucleic acid
    ( C ) STRANDEDNESS: unknown
    ( D ) TOPOLOGY: linear ( i i ) MOLECULE TYPE: Other nucleic acid;
    ( A ) DESCRIPTION: synthetic DNA ( x i ) SEQUENCE DESCRIPTION: SEQ ID NO:8:

GGGAATTCTC NACNCCRTGY TGYTGRCA                                           28

( 2 ) INFORMATION FOR SEQ ID NO:9:

( i ) SEQUENCE CHARACTERISTICS:
    ( A ) LENGTH: 19 base pairs
    ( B ) TYPE: nucleic acid
    ( C ) STRANDEDNESS: unknown
    ( D ) TOPOLOGY: linear ( i i ) MOLECULE TYPE: Other nucleic acid;
    ( A ) DESCRIPTION: synthetic DNA ( x i ) SEQUENCE DESCRIPTION: SEQ ID NO:9:

CATGTCGGAT GTTGTCCAG                                                     19

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:10:

CTGGACAACA TCCGA                                            15